United States Patent
Nguyen et al.

(10) Patent No.: US 12,129,508 B2
(45) Date of Patent: Oct. 29, 2024

(54) PROCESS FOR HYDROLYZING OIL WITH HIGH MELTING POINT BY LIPASE

(71) Applicant: WILMAR INTERNATIONAL LIMITED, Singapore (SG)

(72) Inventors: Kien Truc Giang Nguyen, Singapore (SG); Ren Liang Yang, Singapore (SG)

(73) Assignee: WILMAR INTERNATIONAL LIMITED, Singapore (SG)

( * ) Notice: Subject to any disclaimer, the term of this patent is extended or adjusted under 35 U.S.C. 154(b) by 616 days.

(21) Appl. No.: 17/425,692

(22) PCT Filed: Oct. 2, 2019

(86) PCT No.: PCT/SG2019/050497
§ 371 (c)(1),
(2) Date: Jul. 23, 2021

(87) PCT Pub. No.: WO2020/153902
PCT Pub. Date: Jul. 30, 2020

(65) Prior Publication Data
US 2022/0010341 A1      Jan. 13, 2022

(30) Foreign Application Priority Data
Jan. 25, 2019   (SG) .............................. 10201900696

(51) Int. Cl.
*C12P 7/6454*   (2022.01)
*C12N 9/20*   (2006.01)

(52) U.S. Cl.
CPC .............. *C12P 7/6454* (2013.01); *C12N 9/20* (2013.01); *C12Y 301/01003* (2013.01)

(58) Field of Classification Search
CPC ........ C12P 7/6454; C12P 7/6418; C12N 9/20; C12Y 301/01003; C11C 1/10; C11C 1/045
See application file for complete search history.

(56) References Cited

U.S. PATENT DOCUMENTS

| 2004/0014184 A1 | 1/2004 | Otto et al. |
| 2015/0010966 A1 | 1/2015 | Lali et al. |

FOREIGN PATENT DOCUMENTS

| CN | 108239663 | * | 7/2018 | ............ C12P 7/6418 |
| CN | 108239663 A | | 7/2018 | |
| EP | 2298727 A1 | | 3/2011 | |
| WO | 9103565 A1 | | 3/1991 | |

OTHER PUBLICATIONS

Fu B., Effect of Organic Solvents and Cosolvents On Lipase-Catalyzed Transesterification of Canola Oil . M. Sc., Thesis, Univ. New Hampshire., 2009, pp. 1-131. (Year: 2009).*
Jachmanain et al., Substrate selectivity in esterification of less common fatty acids catalysed by lipases from different sources. Appl . Microbiol., Biotechnol., 1996, vol. 44: 563-567. (Year: 1996).*
Novozymes Eversa Transform 2.0 Lipase. Application data Sheet, 8 pages, downloaded Apr. 24, 2024. (Year: 2024).*
International Search Report issued in PCT/SG2019/050497 mailed Nov. 18, 2019 (five pages).
Written Opinion issued in PCT/SG2019/050497 mailed Nov. 18, 2019 (six pages).

* cited by examiner

*Primary Examiner* — Ganapathirama Raghu
(74) *Attorney, Agent, or Firm* — Studebaker & Brackett PC

(57) ABSTRACT

The present invention is in the field of oil processing, and specifically the present invention relates to a process of hydrolyzing an oil with high melting point, such as hydrogenated castor oil (HCO), by lipase. In an embodiment of the invention, there is provided a process of hydrolyzing an oil having a higher melting point to obtain a hydrolysis product, the process comprising: a step of mixing water, an organic solvent, and a lipase with the oil to form a mixture, and a step of hydrolyzing the oil in the mixture, wherein the lipase comprises one or more lipase derived from *Thermomyces* sp. but not any monoacylglycerol lipase or any lipase derived from *Rhizomucor* sp., and the organic solvent is any one selected from a sterically hindered alcohol, a non-polar organic solvent, and a mixture of a water-miscible organic solvent with a non-polar organic solvent.

15 Claims, No Drawings
Specification includes a Sequence Listing.

PROCESS FOR HYDROLYZING OIL WITH HIGH MELTING POINT BY LIPASE

TECHNICAL FIELD

The present invention is in the field of oil processing, and specifically the present invention relates to a process of hydrolyzing an oil with high melting point, such as hydrogenated castor oil (HCO), by lipase.

BACKGROUND 12-hydroxystearic acid (12-HSA) is an 18-carbon fatty acid having a hydroxyl group at position 12, and its molecular formula is $CH_3(CH_2)_5CH(OH)(CH_2)_{10}COOH$. It is in the form of white to cream-colored flakes or needle crystals at room temperature and has a melting point of 72-77° C. Since 12-HSA contains both a hydroxyl group and a carboxyl group, it has special chemical properties that make it an important raw material for chemical industries. 12-HSA is also used as an intermediate product in the plastic production or as a raw material for cosmetic production.

There are mainly two approaches to prepare 12-HSA. One is to hydrolyze castor oil under high temperature and high pressure to obtain ricinoleic acid first, which is then hydrogenated to 12-HSA. During the hydrogenation process, esterification reaction of the hydroxyl group and the carboxyl group in ricinoleic acid may occur and result in polymerization, which lowers the production yield of 12-HSA. The other approach is to carry out hydrogenation of castor oil first to obtain hydrogenated castor oil (HCO), which is then hydrolyzed by strong alkali and subsequently acidulated with strong acid to prepare 12-HSA. Although this approach can protect the hydroxyl group from being damaged, the method generates a large amount of waste water, thereby causing environmental pollutions.

New developments on the preparation of 12-HSA by enzymatic hydrolysis of HCO have been reported as followings.

CN104946692A discloses a method for the hydrolysis of HCO in the presence of a biohydrolase, wherein HCO and deionized water are mixed in a certain ratio, and three rounds of hydrolysis was conducted to obtain 12-HSA. Each round of hydrolysis is conducted under a mass ratio of "HCO:water:hydrolase=100:60~100:0.3~0.5". The temperature used for the hydrolysis is 80-85° C., and the hydrolysis continued for 120-180 min. The reaction temperature of the method is above 80° C. Since most lipases would lose or reduce their enzyme activities under a temperature higher than 50° C., this method excludes most lipases, and only several thermostable lipases are applicable, which are usually expensive.

JP61139396 also disclosed a process for the preparation of 12-HSA at a temperature of 75° C. It utilizes an organic solvent with water for the dissolution of HCO, and the hydrolysis is catalyzed by a lipase derived from a microorganism belonging to the genus Chromobacterium, *Rhizopus*, *Mucor*, or *Pseudomonas*. This method has the same disadvantage that the reaction is conducted under a high temperature.

CN1473199A also reported a method for preparing 12-HSA: mainly to firstly convert castor oil to ricinoleic acid by one or more lipases at 15-50° C., then the hydrolyzed product is converted to 12-HSA. Although the method has a low operating temperature during the enzymatic hydrolysis process, the method causes a loss of hydroxyl groups and a decrease in the acid value of the final product.

CN108239663A disclosed a method for enzymatic hydrolysis of HCO at low temperature in the presence of a first organic solvent, a second organic solvent and water. The hydrolysis is carried out at 35-55° C., preferably 45-50° C. Any two of lipase from *Thermomyces* sp., lipase from *Rhizomucor* sp. and monoacylglycerol lipase are used in combination to achieve a maximal hydrolysis rate of 86.21%. This method utilizes a combination of lipases in a large amount that causes high cost of the process, and the final hydrolysis rate is still less than 90%.

The above prior art shows the preparation of 12-HSA by various processes, which have various disadvantages, such as the loss of hydroxyl groups, high hydrolysis temperature, limited option of applicable lipases, required use of a plurality of lipases or high cost, etc.

Therefore, there is need to prepare 12-HSA in a cheap and efficient way, such as enzymatic hydrolysis of HCO under low temperature by using common lipase, and achievement of high hydrolysis rate.

SUMMARY

The first aspect of the present invention provides a process for hydrolyzing an oil having a high melting point. Said process comprises a step of mixing water, an organic solvent, and a lipase with said oil to form a mixture, and a step of hydrolyzing the oil in the mixture to obtain a hydrolysis product, wherein the lipase comprises one or more lipase derived from *Thermomyces* sp. but not any monoacylglycerol lipase or any lipase derived from *Rhizomucor* sp.

In one or more embodiments, said oil having a higher melting point has a melting point of 40° C. or higher, preferably 45° C. or higher, or 50° C. or higher. The term "higher melting point" is substitutable with "high melting point".

In one or more embodiments, the oil having a higher melting point is hydrogenated castor oil, and the hydrolysis product is 12-HSA.

In one or more embodiments, the process is for the preparation of 12-HSA, which comprises a step of mixing water, an organic solvent, and a lipase with hydrogenated castor oil (HCO) to form a mixture, and a step of hydrolyzing HCO in the mixture to obtain a hydrolysis product, wherein the lipase comprises one or more lipase derived from *Thermomyces* sp. but not any monoacylglycerol lipase or any lipase derived from *Rhizomucor* sp.

In one or more embodiments, said lipase derived from *Thermomyces* sp. is derived from *Thermomyces lanuginosus*. In one or more embodiments, said lipase derived from *Thermomyces* sp. is selected from EVERSA® Transform 2.0 (EVERSA), Lipase LKT400XL, TLL-SH, derivatives thereof and mixtures thereof.

In one or more embodiments, before the step of mixing, the oil having a higher melting point is firstly grinded to a powder form, or firstly melted.

In one or more embodiments, said powder form has a diameter up to 3 mm, preferably up to 0.5 mm.

In one or more embodiments, the ratio of the volume of liquid lipase added in mL to the weight of HCO in gram is not less than 0.2%, preferably not less than 0.3%, more preferably from 0.3% to 2%, even more preferably from 0.3% to 1%. By using lipase concentration in the liquid lipase solution or lipase activity unit provided in the product sheet of the liquid lipase, the weight or activity units of lipase used could be calculated. Hence, when the lipase is provided and added in solid form, the weight ratio of lipase to HCO could be estimated, for example, the weight ratio is not less than 50 ppm, or not less than 57 ppm, or not less than 75 ppm, or not less than 156 ppm.

In one or more embodiments, the organic solvent is any one selected from a sterically hindered alcohol, a non-polar organic solvent, a mixture of water-miscible organic solvent with non-polar organic solvent.

In one or more embodiments, the non-polar organic solvent is selected from ethers and saturated hydrocarbons containing 5 to 12 carbons or the mixture thereof.

In one or more embodiments, said saturated hydrocarbons are short-chain to mid-chain alkanes and cycloalkanes containing 5 to 12 carbons.

In one or more embodiments, the non-polar organic solvent is selected from isooctane, n-heptane, cyclohexane, n-hexane, methyl tert-butyl ether (MTBE), diethyl ether, n-pentane, cyclopentane, petroleum ether, and or the mixture thereof.

In one or more embodiments, the non-polar organic solvent is selected from isooctane, n-hexane or their mixture.

In one or more embodiments, the steric hindered alcohol is tert-butanol (t-BuOH).

In one or more embodiments, in the mixture of water-miscible organic solvent and non-polar organic solvent, the water-miscible organic solvent is selected from acetone, tert-butanol, and the like, and/or the non-polar organic solvent is selected from n-hexane, isooctane, n-heptane, cyclohexane, and the like.

In one or more embodiments, the volume ratio of water-miscible organic solvent to non-polar organic solvent is less than 50:50, preferably from 20:80 to 50:50, more preferably from 25:75 to 35:65, or from 30:70 to 40:60, most preferably 30:70.

In one or more embodiments, the ratio of the volume of the organic solvent in mL to the weight of HCO in gram (V/W) is more than 75% preferably between 100% and 500%, more preferably between 200% and 500%, even more preferably between 200% and 300%, or between 300% and 400%.

In one or more embodiments, the weight ratio of the amount of water added to said HCO is from 15% to 300%, more preferably from 30% to 250% or from 100% to 300%, even more preferably from 50% to 250%, such as from 150% to 250%.

In one or more embodiments, the hydrolysis is conducted under a temperature of 35-60° C., for example under a temperature of 37-55° C., or 40-55° C., more preferably 45-55° C., even more preferably 45-50° C., and most preferably 50° C.

In one or more embodiments, there is glycerol generated during the step of hydrolyzing oil.

In one or more embodiments, there is optionally a step of removing water, glycerol and organic solvent after the step of hydrolyzing the oil.

In one or more embodiments, a product of the hydrolysis process, i.e. said hydrolysis product, has an acid value (mgKOH/g) of higher than 160, preferably higher than 165, more preferably higher than 170, most preferably higher than 175, after removing water, glycerol and organic solvent.

The second aspect of the present invention provides a product obtained by a process for hydrolyzing an oil having a high melting point, the process comprising a step of mixing water, an organic solvent, and a lipase with the oil to form a mixture, and a step of hydrolyzing the oil in the mixture to obtain a hydrolysis product, wherein the lipase comprises one or more lipases derived from *Thermomyces* sp. but not any monoacylglycerol lipase or any lipase derived from *Rhizomucor* sp., preferably said lipase derived from *Thermomyces* sp. is a lipase derived from *Thermomyces lanuginosus*, more preferably is selected from EVERSA, Lipase LKT400XL, TLL-SH, derivatives thereof and mixtures thereof.

The third aspect of the present invention provides a use of lipase in the hydrolysis of oil having higher melting point, or in the preparation of 12-HSA from HCO, wherein the lipase comprises one or more lipases derived from *Thermomyces* sp. but not any monoacylglycerol lipase or any lipase derived from *Rhizomucor* sp., preferably lipase derived from *Thermomyces* sp. is a lipase derived from *Thermomyces lanuginosus*, more preferably is selected from EVERSA, Lipase LKT400XL, TLL-SH, derivatives thereof and mixtures thereof.

The forth aspect of the present invention provides a reaction mixture, which comprises an oil with high melting point, an organic solvent, water and a lipase, wherein the lipase comprises one or more lipases derived from *Thermomyces* sp. but not any monoacylglycerol lipase or any lipase derived from *Rhizomucor* sp.; preferably said lipase derived from *Thermomyces* sp. is a lipase derived from *Thermomyces lanuginosus*, more preferably is selected from EVERSA, Lipase LKT400XL, TLL-SH, derivatives thereof and mixtures thereof.

DETAILED DESCRIPTION

The following detailed description refers to specific details and embodiments in which the invention may be practiced. These embodiments are described in sufficient detail to enable those skilled in the art to practice the invention. Other embodiments may be utilized and various changes may be made without departing from the scope of the invention.

In the context of various embodiments, the term "about" or "approximately" as applied to a numeric value encompasses the exact value and a reasonable variance.

In the context of various embodiments, unless otherwise specified, a range expressed by "from A to B" or "between A and B" includes two endpoint values.

As used herein, the term "and/or" includes any and all combinations of one or more of the associated listed items.

The present invention aims to improve the enzymatic hydrolysis rate of oil with high melting point, increase the acid value of the final products, and shorten the reaction time for achieving similar acid value. The hydrolysis of oil with high-melting-point is carried out under a low temperature by utilizing a lipase, and the final hydrolysis rate can be remarkably improved that it can even directly meet with final product specification. In the current industry practice, enzymatic hydrolysis product from hydrolyzing oil with high-melting-point, such as HCO, usually could not meet with final product specification, and further hydrolysis step is needed.

In the present invention, "high melting point" is substitutable with "higher melting point". "High melting point" or "higher melting point" means a melting point of 40° C. or higher, preferably 45° C. or higher, or 50° C. or higher. In the present invention, "oil with high melting point" are for example, HCO, palm stearin, lard, and so on. In the present invention, "oil substrate" means "oil with high melting point".

In particular, the invention relates to the hydrolysis of HCO for the preparation of, 12-HSA. A lipase comprising one or more lipases derived from *Thermomyces* sp. but not any monoacylglycerol lipase or any lipase derived from *Rhizomucor* sp. is used for the hydrolysis.

In one or more embodiments, the lipase derived from *Thermomyces* sp. could be derived from *Thermomyces lanuginosus, Thermomyces dupontii, Thermomyces stellatus, Thermomyces ibadanesis* etc.

In one or more embodiments, the lipase derived from *Thermomyces* sp. is a lipase derived from *Thermomyces lanuginosus*, for example, EVERSA Transform 2.0 (EVERSA) which is a lipase derived from *Thermomyces lanuginosus* and produced in *Aspergillus oryzae*, or other lipases derived from *Thermomyces* sp. and having similar enzyme characteristics to EVERSA, such as Callera Trans® L by Novozymes, Lipozyme® TL 100L or Lipolase® by Novozymes, Lipase NS-40116 by Novozymes, Lipase LKT400XL by Leveking (Shenzhen).

In one or more embodiments, the lipase derived from *Thermomyces* sp. is selected from EVERSA, Lipase LKT400XL, TLL-SH, derivatives thereof and mixtures thereof.

Lipase LKT400XL is a commercially available product that has lipase with more than 99% identity with the lipase in Callera Trans® L which is a liquid formulation of *Thermomyces lanuginosus* lipase provided by Novozymes. TLL-SH is a lipase obtained by expressing a wild lipase sequence from *Thermomyces lanuginosus* in *Pichia pastoris*.

As used herein, the term "derivative" means the enzyme is resulted from substituting, deleting or adding one or more amino acids to the amino acid sequence of an enzyme while retaining the lipase activity of the polypeptides. "More" herein means less than 20, preferentially less than 10, more preferentially less than 8, and even more preferentially less than 5. The term "derived from" means an enzyme is a wild type polypeptide from the specific specie or a natural or artificial derivative of the wild type polypeptide.

When it is used in the process of the present invention, the lipase derived from *Thermomyces* sp. could be added once or in batch. The lipase could also be recycled and reused in the process, for example, the aqueous layer of the reaction mixture could be collected and re-added to the mixture after some reaction by-products are removed. When the lipase is commercially provided in liquid form or solution form, it is added in liquid form. The amount of said lipase in liquid form added is not less than 0.2% volume to weight ratio (V/W, mL/g) of the oil substrate, for example, not less than 0.3%, such as 0.3% to 2%, preferably 0.3% to 1%, or 0.5% to 1%, or 0.75% to 1%, or 0.8% to 1%, or 0.3% to 0.5%, or 0.3%. By using lipase concentration or lipase activity unit provided in the corresponding product sheet, the weight or activity units of lipase used could be calculated. Hence, when the lipase is provided and added in solid form, the weight ratio of lipase to HCO could be estimated, for example, the weight ratio of lipase to the oil substrate could be not less than 50 ppm or not less than 57 ppm, not less than 75 ppm, not less than 125 ppm, not less than 156 ppm, not less than 250 ppm. Preferably the lipase in solid form used is in the range selected from 57 ppm to 380 ppm, from 95 ppm to 380 ppm, from 152 ppm to 380 ppm, from 142.5 ppm to 190 ppm, from 152 ppm to 190 ppm, from 50 ppm to 500 ppm, from 75 ppm to 500 ppm, from 75 ppm to 250 ppm, or from 250 ppm to 500 ppm, from 156 ppm to 1040 ppm, from 260 ppm to 1040 ppm, from 260 ppm to 520 ppm or any combination of the ranges.

Optionally, the oil with high melting point is firstly milled to a powder form before the step of mixing. In one or more embodiments, the powder form has a size of smaller than 0.5 millimeter in diameter. The size of the powder form could be measured by using optical microscope or sieving method. By adding oil substrate in a powder form, the surface area of the oil substrate is increased and the interaction between oil and enzyme is improved, thus less enzyme is required.

The milling of the oil could be done in common ways, such as manually using mortar and pestle, mechanically using grinder or home blender, or the like.

Optionally, the oil with high melting point is firstly melted before the step of mixing.

The hydrolysis is conducted in the presence of organic solvent(s). One or more organic solvents could be added to the hydrolysis process. Organic solvent that could be used in the process of the present invention is selected from a non-polar organic solvent, a steric hindered alcohol, mixtures thereof and a mixture of a water-miscible organic solvent and a non-polar solvent.

Polar solvents are solvents that have large dipole moments, i.e. partial charges, so contain bonds between atoms with very different electronegativities, such as oxygen and hydrogen.

In one or more embodiments, the steric hindered alcohol is tert-butanol (t-BuOH).

In one or more embodiments, the non-polar organic solvent is ethers and saturated hydrocarbons containing 5 to 12 carbons or the mixture thereof.

In one or more embodiments, said saturated hydrocarbons are short-chain to mid-chain alkanes and cycloalkanes containing 5 to 12 carbons.

In one or more embodiments, the non-polar organic solvent is selected from isooctane, n-heptane, cyclohexane, n-hexane, methyl tert-butyl ether (MTBE), diethyl ether, n-pentane, cyclopentane, petroleum ether, and or the mixture thereof.

Preferably, the organic solvent is n-hexane or isooctane or their mixture. In one or more embodiments, the ratio of the volume of organic solvent in mL to the weight of HCO in gram (V/W) is more than 75%, preferably, between 100% and 500%, more preferably between 200% and 500%, even more preferably between 200% and 300%, or between 300% and 400%.

Preferably, ethers (such as MTBE) is added as the organic solvent. By optimizing reaction conditions, final products with acid values of higher than 160, or higher than 170 could be obtained.

Preferably, steric hindered alcohol (such as t-BuOH) is added as the organic solvent.

In one or more embodiments, the organic solvent is a mixture of water-miscible organic solvent and non-polar organic solvent.

Water-miscible organic solvents are those which can be mixed with water in all proportions, forming a homogeneous solution. A possible function that water-miscible organic solvent performs in said mixture is to promote the interaction between the organic phase and aqueous phase, thereby promote the interaction between oil substrate and lipase and accelerate hydrolysis.

Said water-miscible organic solvent is selected from acetone, t-BuOH, and the like.

In one or more embodiments, in the mixture of organic solvents, the volume ratio of water-miscible to non-polar organic solvents is less than 50:50, preferably from 20:80 to 50:50, more preferably from 25:75 to 35:65, or from 30:70 to 40:60, most preferably 30:70.

Preferably, a mixture of t-BuOH or acetone with n-hexane or isooctane is added as the organic solvent. By optimizing reaction conditions, final products with acid values of higher than 160, or higher than 170 could be obtained. The ratio of total volume of the mixture of organic solvents by mL to the quantity of HCO by gram is from 100% to 300%, preferably, from 150% to 200%.

Hydrolysis of oil with high melting point, such as HCO, is conducted in the presence of water. Usually the amount of water could be determined according to the amount of enzyme and/or the amount of oil substrate and/or the type/amount of organic solvent added. When non-polar organic solvent is added, usually the weight ratio of water to the oil substrate is from 15% to 300% or from 30% to 250% or from 50% to 250%. When a mixture of water-miscible and non-polar organic solvent is added, the weight ratio of water to said HCO is from 100% to 300%, preferably from 150% to 250%. For the best hydrolysis effect, a person skilled in the art could adjust the ratio between oil and water according to the amount of the enzyme used, reaction temperature, the type/amount of solvent used, reaction time, and so on.

Similarly, suitable amount of organic solvent could be adjusted according to the amounts of other reagents used.

To carry out the hydrolysis procedure of the present invention, the oil substrate is milled into a powder form, then the powder is mixed with water and organic solvent(s), and subsequently the lipase is added, and mixed well. The mixing could be done by vortexing, stirring by a stir bar or the like, such as stirring at 450 rpm. If lipase is added in liquid solution form, preferably water contained in the lipase solution is calculated to be deducted from the water added to the mixture, so that the weight ratio of water to oil substrate is within the range specified above.

The hydrolysis is usually carried out under a temperature of 35-60° C., such as 37-55° C., or 40-55° C., more preferably 45-55° C., even more preferably 45-50° C., and most preferably 50° C. When oil substrate and other reagents are mixed, the temperature of the mixture is gradually elevated to a temperature in the range of 35~60° C. for the hydrolysis to be carried out. Usually the temperature is elevated while mixing. The stirring could be continued through the hydrolysis process. Alternatively, the oil substrate could be melted firstly under a temperature slightly higher than the melting point of the oil substrate, then the melted oil substrate is slowly mixed with the water and organic solvent(s) (which are pre-chilled if the melting point of the oil substrate is very high, such as higher than 80° C.) by stirring or vortexing to bring the system temperature to 35~60° C. Then lipase is added and the hydrolysis is carried out. The stirring could be continued through the hydrolysis process.

The time needed for the hydrolysis is not narrowly limited. According to the weight of the oil substrate, the type of lipase and the amount of the lipase added, the hydrolysis time could be determined. Alternatively, samples could be taken along the process of the hydrolysis and be analyzed, for example, to get acid values of the samples. When the acid value or the hydrolysis rate reaches a certain value, the reaction could be stopped.

In some embodiments, the reaction time is less than 80 hours, preferably no more than 72 hours, such as 48 hours, 36 hours, or 24 hours.

Direct product of the reaction often has an acid value of higher than 160 after removing water, glycerol and organic solvent, preferably higher than 165 after removing water, glycerol and organic solvent, more preferably higher than 170, even more preferably higher than 175, after removing water, glycerol and organic solvent, most preferably higher than 180. The hydrolysis rate of the reaction could be calculated by using acid values from the beginning of the reaction and the end of the reaction.

In one or more embodiments, Lipase LKT400XL was used to catalyze the hydrolysis of HCO at a temperature of higher than 40° C., such as between 45° C. to 55° C., for example 50° C. By adding saturated hydrocarbons containing 5 to 12 carbons, such as n-hexane or isooctane, as the organic solvent, acid values of the final product after removing water, glycerol and solvent are higher than 165, corresponding to hydrolysis rate of higher than 87.3%. Preferably, the ratio of solvent volume in mL to the HCO weight in gram is in the range of from 100% to 500%. More preferably, the ratio of said saturated hydrocarbons volume in mL to the HCO weight in gram is in the range of from 200% to 500%, such as from 200% to 300% or 200%, for achieving acid values of higher than 170, or even higher than 175, i.e. between 175 and 185.

In one or more embodiments, ethers (such as MTBE) is added as the organic solvent for the hydrolysis catalyzed by Lipase LKT400XL. By optimizing reaction conditions, final products with acid values of higher than 165 were obtained.

In one or more embodiments, steric hindered alcohol (such as t-BuOH) is added as the organic solvent for the hydrolysis catalyzed by Lipase LKT400XL. By optimizing reaction conditions, final products with acid values of higher than 160, or higher than 170 could be obtained.

In one or more embodiments, a mixture of t-BuOH or acetone with n-hexane or isooctane is added as the organic solvent for the hydrolysis catalyzed by Lipase LKT400XL. By optimizing reaction conditions, acid values of the final product after removing water, glycerol and solvent are higher than 165.

In one or more embodiments, when the water amount is in the range of from 50% to 150%, the acid values obtained are basically higher than 165.

In one or more embodiments, Lipase LKT400XL is added as commercially provided. Under optimized reaction conditions, when the amount of LKT400XL solution used by volume in mL is not less than 0.3% (V/W) of the weight of HCO in gram, reaction product with acid values of higher than 175 could be obtained, for example from 0.3% to 2%, more preferably from 0.5% to 2%, even more preferably from 0.8% to 2%, and even more preferably from 0.75% to 1% or from 0.8% to 1%. By using Bradford assay, the protein concentration in Lipase LKT400XL is determined to be 19 mg/mL, thus if lipase is added in dry solid form, the amount of protein or lipase required could be estimated. When added in solid form, the amount of lipase added is not less than 57 part per million (ppm, related to the weight of HCO), acid values of higher than 175 could be achieved, such as from 57 ppm to 380 ppm, more preferably from 95 ppm to 380 ppm, even more preferably from 152 ppm to 380 ppm, and even more preferably from 142.5 ppm to 190 ppm or from 152 ppm to 190 ppm.

In one or more embodiments, lipase EVERSA was added as commercially provided to catalyze the hydrolysis of HCO at a temperature of higher than 40° C., such as between 45° C. and 55° C. By adding saturated hydrocarbons containing 5 to 12 carbons, such as n-hexane or isooctane, as the organic solvent, acid values of the final products after removing water, glycerol and solvent are higher than 160. Preferably, the ratio of solvent volume in mL to the HCO weight in gram is in the range of from 100% to 500%. More preferably, the ratio of C5-C12 alkane volume in mL to the HCO weight in gram is in the range of from 200% to 500%, such as from 300% to 400%, for achieving acid values of higher than 170, or even higher than 175, i.e. around 180.

In one or more embodiments, steric hindered alcohol (such as t-BuOH) is added as the organic solvent for the hydrolysis catalyzed by EVERSA. By optimizing reaction conditions, final products with acid values of higher than 160, or higher than 170 could be obtained. The preferred water amount is 100% or from 300% to 500% (V/W, mL/g) or the weight of HCO.

In one or more embodiments, ethers (such as MTBE) is added as the organic solvent. By optimizing reaction conditions, final products with acid values of higher than 160, or higher than 170 could be obtained. For example, when 200% (V/W, mL/g of HCO) of MTBE, EVERSA in an amount of 1% (V/W, mL/g of HCO), and water amount in a range of higher than 100% were applied, acid values of higher than 160 were obtained. More specially, when water amount was from 100% to 300%, preferably around 200%, acid values of higher than 171 were obtained.

In one or more embodiments, a mixture of t-BuOH or acetone with n-hexane or isooctane is added as the organic solvent. By optimizing reaction conditions, final products with acid values of higher than 160, or higher than 170 could be obtained. For example, the water amount added is around 250% (V/W, mL/g) to the weight of HCO.

In one or more embodiments, water amount used is in the range of from 50% to 200%, and acid values obtained are basically higher than 165. Preferably, the water amount is in the range of from 50% to 100%, from 100% to 150%, or from 100% to ~200%, such as from 75% to 100%.

In one or more embodiments, under optimized reaction conditions, when the amount of EVERSA used was not less than 0.2%, or not less than 0.3%, or not less than 0.5%, especially not less than 1%, reaction products with acid values of higher than 170, or higher than 175, or even near 180 could be obtained. Overall 1% EVERSA could guarantee acid value of the hydrolysis product to be higher than 175, or higher than 180. The amount of EVERSA solution used in mL is not less than 0.2% (V/W) of the weight of HCO in gram, preferably from 0.2% to 2%, more preferably from 0.3% to 2%, even more preferably from 0.3% to 1%, or from 1% to 2%. By using Bradford assay, the protein concentration in EVERSA is determined to be 25 mg/mL, thus if lipase is added in dry solid form, the amount of protein or lipase required could be estimated. When added in solid form, when the amount of lipase added is not less than 50 ppm, or not less than 75 ppm, or not less than 125 ppm, or not less than 250 ppm, acid values of higher than 170, or higher than 175, or even near 180 could be achieved. The amount of solid lipase used is not less than 50 ppm, preferably from 50 ppm to 500 ppm, more preferably from 75 ppm to 500 ppm, even more preferably from 75 ppm to 250 ppm, or from 250 ppm to 500 ppm.

In one or more embodiments, other lipase derived from *Thermomyces* sp. or from *Thermomyces lanuginosus*, such as TLL-SH, was used to catalyze the hydrolysis of HCO. TLL-SH is a lipase obtained by expressing a wild lipase sequence from *Thermomyces lanuginosus* in *Pichia pastoris*. By optimizing ratios and reaction conditions, hydrolysis products with AV higher than 175 could be easily obtained with a dosage of 1% TLL-SH, and hydrolysis products with AV higher than 170 could be obtained with a dosage of 0.5% TLL-SH. Temperature for the reaction is between 37° C. and 55° C., preferably between 4° and 55° C., more preferably between 45° C. and 55° C., most preferably 50° C.; the organic solvent is n-hexane, isooctane, MTBE, t-BuOH, or a mixture of t-BuOH or acetone with n-hexane or isooctane. The amount of solvent and water used could be adjusted according to common technology in the field. The amount of TLL-SH solution used is not less than 0.3% of the weight of HCO, preferably from 0.3% to 2%, more preferably from 0.5% to 2%, even more preferably from 0.5% to 1%. The weight of TLL-SH used could be calculated by using its protein concentration determined by the Bradford assay. If TLL-SH is added in solid form, the amount added is not less than 156 ppm, preferably from 156 ppm to 1040 ppm, more preferably from 260 ppm to 1040 ppm, even more preferably from 260 ppm to 520 ppm.

In the preparation of 12-HSA from HCO by hydrolysis, the 12-HSA could be separated and purified by vacuum distillation.

The present invention also provides a use of lipase in the hydrolysis of oil with high melting point, in the preparation of 12-HSA from HCO, and in the reaction mixture of hydrolysis of oil with high melting point or hydrolysis of HCO for the preparation of 12-HSA. In some embodiments, the lipase comprises one or more lipase derived from *Thermomyces* sp. but not any monoacylglycerol lipase or any lipase derived from *Rhizomucor* sp.; preferably said lipase derived from *Thermomyces* sp. is a lipase derived from *Thermomyces lanuginosus*, more preferably is selected from EVERSA, Lipase LKT400XL, TLL-SH, derivatives thereof and mixtures thereof. In some embodiments, the lipase is added in liquid form as commercially provided, and the amount of lipase used is not less than 0.3% volume to weight (V/W, mL/g) ratio (for lipase solution) or weight ratio of the oil substrate, for example, the amount used is 0.3% to 2%, preferably 0.3% to 1%, or 0.5% to 1%, or 0.75% to 1%, or 0.8% to 1%, or 0.3% to 0.5%, or 0.3%. By using lipase concentration or lipase activity unit provided in the corresponding product sheet, the weight or activity units of lipase used could be calculated. Hence, when the lipase is provided and added in solid form, the weight ratio of lipase to HCO could be estimated, for example, the weight ratio of lipase to the oil substrate could be not less than 50 ppm or not less than 57 ppm, not less than 75 ppm, not less than 125 ppm, not less than 156 ppm, not less than 250 ppm. Preferably the lipase in solid form used is in the range selected from 57 ppm to 380 ppm, from 95 ppm to 380 ppm, from 152 ppm to 380 ppm, from 142.5 ppm to 190 ppm, from 152 ppm to 190 ppm, from 50 ppm to 500 ppm, from 75 ppm to 500 ppm, from 75 ppm to 250 ppm, or from 250 ppm to 500 ppm, from 156 ppm to 1040 ppm, from 260 ppm to 1040 ppm, from 260 ppm to 520 ppm or any combination of the ranges. In some embodiments, the amount of organic solvents, the amount of water, and the amount of lipase, and the ratio thereof are added as stated above.

The present invention also provides a reaction mixture, wherein the mixture comprises oil with high melting point, organic solvent(s), water and lipase; wherein the lipase comprises one or more lipases derived from *Thermomyces* sp., but not any monoacylglycerol lipase or any lipase derived from *Rhizomucor* sp.; preferably said lipase derived from *Thermomyces* sp. is a lipase derived from *Thermomyces lanuginosus*, more preferably is selected from EVERSA, Lipase LKT400XL, TLL-SH, derivatives thereof and mixtures thereof. In some embodiments, the amount of oil substrate, the amount of organic solvent(s), the amount of water, and the amount of lipase, and the ratio thereof are added as stated above. In some embodiments, the reaction mixture is for the preparation of 12-HSA. In some embodiments, the reaction mixture is the mixture in the procedure of the present invention for the preparation of 12-HSA, wherein the reaction mixture might contain 12-HSA.

By utilizing the procedure and the reaction mixture of the present invention, a final product with an acid value of more than 160 mgKOH/g could be obtained after removing water, glycerol and organic solvent; more preferably, a final product with an acid value of more than 175 mgKOH/g could be obtained after removing water, glycerol and organic solvent. The hydrolysis rate of the reaction could be calculated by using the acid value at the beginning of the reaction and at the end of the reaction. At least a hydrolysis rate of more than 60% could be obtained by using the procedure of the present invention and the reaction mixture of the present invention. More preferably, a hydrolysis rate of more than 70% could be achieved, such as a hydrolysis rate of more than 75%. More preferably, a hydrolysis rate of more than 80% could be achieved, such as a hydrolysis rate of more than 85%. Even more preferably, a hydrolysis rate of more than 90% could be achieved, such as a hydrolysis rate of more than 95%. Most preferably, a hydrolysis rate of more than 97% or more than 98% is achieved.

EXAMPLES

In the following text, the present invention is illustrated in further details by the following non-limiting examples. The HCO used in the examples below is purchased from Wilmar Oleochemicals Co., Ltd, China, and its melting point is from 82° C. to 88° C. Fine powder form of HCO is obtained by grinding the HCO flakes with home use blender or manually grinding with mortar and pestle. N,N-dimethylformamide (DMF), MTBE, diethyl ether and tert-butanol inanalytical reagent grade were purchased from Sigma-Aldrich Singapore; n-heptane in analytical reagent grade was purchased from Schedelco; cyclohexane and isooctane in analytical reagent grade were purchased from Fisher Singapore; acetonitrile in HPLC grade was purchased from Fisher Singapore; n-hexane in industrial grade was purchased from Aik Moh Paints & Chemicals Pte Ltd Singapore.

The lipases: lipase B *Candida antarctica* (CalB, #L3170, ≥5,000 LU/g), lipase A *Candida antarctica* (CalA, #L3420, ≥6,000 LU/g), lipase from *Thermomyces lanuginosus* (TLL, #L0777, ≥100,000 U/g, Lipolase of Novozymes) and lipase from *Rhizomucor miehei* (RML, #L4277, ≥20,000 U/g) were purchased from Sigma-Aldrich Singapore and provided in solution form. Amano Lipases (AL) M from *Mucor javanicus* (#534803, ≥10,000 U/g), AL AK from *Pseudomonas fluorescens* (#534730, ≥20,000 U/g), AL G from *Penicillium camemberti* (#534838, ≥50,000 U/g), AL A from *Aspergillus niger* (#534781, ≥12,000 U/g), and AL PS from *Burkholderia cepacia* (#534641, ≥30,000 U/g) were purchased from Sigma-Aldrich Singapore and provided in powder form; ResinaseHT solution (>50 KLU/g) was from Novozymes; EVERSA was obtained from Novozymes in liquid form with a concentration of 25 mg/mL (determined by Bradford assay) and an activity of ≥100 LCLU/g; Lipase LKT400XL was from Leveking, Shenzhen, China in liquid form with a concentration of 19 mg/mL (determined by Bradford assay) and an activity of 500,000 U/mL. Lipase LKT400XL has more than 99% identity with the lipase Callera Trans® L which is a liquid formulation of *Thermomyces lanuginosus* lipase provided by Novozymes.

Preparation process for TLL-SH and G50-SH is shown in Example 11. TLL-SH solution has a protein concentration of 52 mg/mL, and G50-SH has a protein concentration of 19.5 mg/mL. The protein concentration was determined by Bradford assay.

The lipase enzymes were added in liquid form, if not specified, and the amount of lipase added to the hydrolysis reaction was calculated by volume (in mL) to the weight of the oil substrate (in gram); if lipase was commercially provided in solid powder form, the amount of lipase added to the hydrolysis reaction was calculated by weight percentage to the oil substrate. If not otherwise specified; the percentage in the present specification is weight percentage.

In the examples, the hydrolysis rate was calculated according to the following formula:

$$\text{Hydrolysis rate} = \frac{AV_t - AV_0}{SV - AV_0} \times 100\%$$

Wherein, $AV_0$ is the acid value of the oil substrate, which is determined to be 1.04 mgKOH/g for HCO used in the present application; $AV_t$ is the acid value of the hydrolysis product at time t; SV refers to the saponification value of the hydrolyzed/hydrolysis product 12-HSA which is determined to be 188.93 mgKOH/g in the present application by using AOCS Cd 3-25 method.

The acid value (AV, mgKOH/g) of the hydrolysis product is determined by evaporating the organic solvent completely with rotary evaporator, washing the melted residue with water at 90° C.-95° C. to remove glycerol, and then titrating the completely dried water-washed hydrolysis product with standard KOH solution using AOCS Da 14-48 method.

Example 1. Comparison of Lipases for the Hydrolysis of HCO 5 grams of HCO in the form of fine powder was put into a reactor, then deionized water was added to the amount of 25% of the oil weight (including water in the enzyme solution), and 25 mL of isooctane as organic solvent (the ratio of "the volume of organic solvent in mL to the weight of oil in gram (V/W)" was 500%) was added into the reactor. Then 100 μL of enzyme solution if provided in solution form or 100 mg of enzyme powder if commercially provided in powder form was added into the mixture as shown in the Table 1 below. The mixture was heated with a stirring rate of 450 rpm to the reaction temperature of 37° C. The stirring was continued through the reaction, and the reaction time was 24 or 72 hours. After the completion of the reaction, acid values (AV) were determined and shown in Table 1 below.

TABLE 1

Lipases for the hydrolysis of HCO

| Exp. No. | 1 | 2 | 3 | 4 | 5 | 6 | 7 |
|---|---|---|---|---|---|---|---|
| Enzyme | CalB | CalA | TLL | Eversa | RML | AL M | TLL-SH |
| AV | 22.52 (24 h) | 44.59 (24 h) | 59.0 (24 h) | 107.80 (24 h) | 50.09 (24 h) | 40.15 (24 h) | 175.66 (72 h) |

| Exp. No. | 8 | 9 | 10 | 11 | 12 | 13 | |
|---|---|---|---|---|---|---|---|
| Enzyme | AL A | AL AK | AL G | AL PS | Resinase HT | LKT400XL | N/A |
| AV | 11.38 (24 h) | 45.24 (24 h) | 5.71 (24 h) | 55.08 (24 h) | 45.93 (72 h) | 107.85 (24 h) | |

Table 1 shows TLL, EVERSA, RML and AL PS, LKT400XL and TLL-SH were able to obtain hydrolysis product with an acid value of more than 50 after 24 hours. EVERSA and LKT400XL were very efficient that their hydrolysis products achieved an acid value of 107.8 after 24 hours of reaction, and TLL-SH was able to achieve an acid value of 175.66 after 72 hours of reaction.

Example 2-Hydrolysis of HCO by lipase LKT400XL 2.1 the Effect of n-Hexane Amount on the Hydrolysis Catalysed by Lipase LKT400XL 5 grams of HCO in the form of fine powder was put into a reactor, then deionized water was added to the amount of 50% (V/W) of the oil weight (including water present in the enzyme solution), and 5, 10, 15 or 25 mL of n-hexane (the ratio of "the volume of organic solvent in mL to the weight of oil in gram (V/W)" was 100%, 200%, 300% or 500%) were added into the reactor. Then 100 μL lipase LKT400XL (2% (V/W) of HCO) was added into the mixture. The mixture was heated with a stirring rate of 450 rpm to the reaction temperature of 45° C. The stirring was continued through the reaction, and the reaction lasted for 72 hours. After the completion of the reaction, the acid values were determined and shown in the Table 2 below.

TABLE 2

Different amount of n-hexane for the hydrolysis of HCO by LKT400XL

| Exp. No. | 14 | 15 | 16 | 17 |
|---|---|---|---|---|
| HCO Powder | | 5 g | | |
| n-Hexane, mL | 5 | 10 | 15 | 25 |
| water | | 2.5 mL | | |
| Temp. | | 45° C. | | |
| LKT400XL | | 100 μL, 2% (V/W) of HCO | | |
| AV (72 h) | 168.11 | 179.23 | 172.68 | 175.64 |
| Hydrolysis rate, % | 88.92 | 94.84 | 91.35 | 92.93 |

By using n-hexane as the organic solvent, acid values of the final product could reach higher than 165. When the ratio of n-hexane volume in mL to the HCO weight in gram was in the range of from 100% to 500%, acid values of higher than 165 were achieved, corresponding to hydrolysis rate of higher than 87.3%; And when the ratio was in the range of from 200% to 500%, acid values of higher than 170 were achieved, corresponding to hydrolysis rate of higher than 88.95%; even acid values of higher than 175 were achieved, which directly meets with AV in the product specification of 12-HSA, i.e. between 175 and 185.

2.2 the Effect of Water Amount on the Hydrolysis Catalysed by Lipase LKT400XL with n-Hexane as the Organic Solvent Experiments 18 to 21 were conducted as described in 2.1, except that different amount of deionized water was added to the amount of 15%, 25%, 150%, 200% of the oil weight (including water present in the enzyme solution), and 10 mL of n-hexane (the ratio of "the volume of organic solvent in mL to the weight of oil in gram (V/W)" was 200%) was added. After the completion of the reaction, the acid values were determined and shown in the Table 3 below.

TABLE 3

Different amount of water for the hydrolysis of HCO by LKT400XL with n-hexane

| Exp. No. | 18 | 19 | 15 | 20 | 21 |
|---|---|---|---|---|---|
| HCO powder | | | 5 g | | |
| n-Hexane | | | 10 mL | | |
| Water | 750 μL | 1.25 mL | 2.5 mL | 7.5 mL | 10 mL |
| LKT400XL | | | 100 μL, 2% (V/W) of HCO | | |
| Temp. | | | 45° C. | | |

TABLE 3-continued

Different amount of water for the hydrolysis of HCO by LKT400XL with n-hexane

| Exp. No. | 18 | 19 | 15 | 20 | 21 |
|---|---|---|---|---|---|
| AV (72 h) | 126.85 | 145.05 | 179.23 | 173.62 | 160.39 |
| Hydrolysis rate, % | 66.96 | 76.65 | 94.84 | 91.85 | 84.80 |

Water amount in the range of more than 25% and no more than 200% of the HCO weight was helpful for achieving acid values higher than 160. When the water amount was in the range of from 50% to 150%, the acid values obtained were basically higher than 165, corresponding to hydrolysis rate of higher than 87.3%.

2.3 the Effect of Temperature on the Hydrolysis Catalysed by Lipase LKT400XL with n-Hexane as the Organic Solvent Experiments 22 to 26 were conducted as described in 2.1, except that deionized water was added to the amount of 150% of the oil weight (including water present in the enzyme solution), and 10 mL of n-hexane as organic solvent (the ratio of "the volume of organic solvent in mL to the weight of oil in gram (V/W)" was 200%) and 50 μL lipase LKT400XL (1% V/W of HCO) was added. The hydrolysis reactions were undergone at different temperature while stirring at 450 rpm. The stirring was continued through the reaction, and the reaction time was 72 hours. After the completion of the reaction, the acid values were determined and the hydrolysis rates were calculated and shown in Table 4.

TABLE 4

Different temperatures for the hydrolysis of HCO by LKT400XL with n-hexane

| Exp. No. | 22 | 23 | 24 | 25 | 26 |
|---|---|---|---|---|---|
| HCO Powder | | | 5 g | | |
| n-Hexane | | | 10 mL | | |
| water | | | 7.5 mL | | |
| LKT400XL | | | 50 μL, 1% (V/W) of HCO | | |
| Temp. (° C.) | 37 | 40 | 45 | 50 | 55 |
| AV (72 h) | 105.12 | 119.31 | 146.79 | 176.64 | 151.38 |
| Hydrolysis rate, % | 55.39 | 62.95 | 77.57 | 93.46 | 80.01 |

When the reaction was conducted under a temperature of higher than 40° C., final products with higher acid values were obtained. Especially when the temperature was between 45° C. and 55° C., higher acid values were obtained.

2.4 the Effect of Enzyme Dosage on the Hydrolysis Catalysed by Lipase LKT400XL with n-Hexane as the Organic Solvent Experiments 27 to 30 were conducted as described in 2.3, except that reaction temperature was 50° C., and different amount of Lipase LKT400XL (100 μL, 37.5 UL, 25 μL or 15 μL corresponding to 2%, 0.75%, 0.5% or 0.3% (V/W) of HCO) was added into the mixture. After the completion of the reaction, acid values were determined and hydrolysis rates were calculated as shown in Table 5.

TABLE 5

Different dosage of enzyme for the hydrolysis of HCO by LKT400XL with n-hexane

| Exp. No. | 27 | 25 | 28 | 29 | 30 |
|---|---|---|---|---|---|
| HCO powder | | | 5 g | | |
| n-Hexane | | | 10 mL | | |
| Water | | | 7.5 mL | | |
| LKT400XL, % (V/W) of HCO | 2% | 1% | 0.75% | 0.50% | 0.30% |
| Temp. | | | 50° C. | | |
| AV (72 h) | 179.73 | 176.64 | 176.38 | 144.84 | 122.35 |
| Hydrolysis rate, % | 95.10 | 93.46 | 93.32 | 76.53 | 64.56 |

When the amount of enzyme used was more than 0.5% (V/W) of HCO, especially not less than 0.75%, hydrolysis product with an acid value of higher than 175 could be obtained.

2.5 the Effect of Isooctane Amount on the Hydrolysis Catalysed by Lipase LKT400XL 5 grams of HCO in the form of fine powder was put into a reactor, then 2.5 mL of deionized water was added to the amount of 50% of the oil weight (including water in the enzyme solution), and 5, 10, 15 or 25 mL of isooctane as the organic solvent (the ratio of "the volume of organic solvent in mL to the weight of oil in gram (V/W)" was 100%, 200%, 300% or 500%) was added into the reactor. Then 100 μL lipase LKT400XL (2% (V/W) of HCO) was added into the mixture. The mixture was heated with a stirring rate of 450 rpm to the reaction temperature of 45° C. The stirring was continued through the reaction, and the reaction time was 72 hours. After the completion of the reaction, the acid values were determined and hydrolysis rates were calculated and shown in Table 6.

TABLE 6

Different amount of isooctane for the hydrolysis by LKT400XL

| Exp. No. | 31 | 32 | 33 | 34 |
|---|---|---|---|---|
| HCO powder | | 5 g | | |
| Isooctane | 5 mL | 10 mL | 15 mL | 25 mL |
| water | | 2.5 mL | | |
| Temp. | | 45° C. | | |
| LKT400XL | | 100 μL, 2% (V/W) of HCO | | |
| AV (72 h) | 159.31 | 178.42 | 177.19 | 175.10 |
| Hydrolysis rate (%) | 84.24 | 94.41 | 93.75 | 92.64 |

When the ratio of isooctane volume in mL to the HCO weight in gram was bigger than 100%, acid values of higher than 160 were achieved. Especially, when the ratio was between 200% and 500%, acid values of higher than 175 were obtained, corresponding to hydrolysis rates of higher than 92.59%.

2.6 the Effect of Water Amount on the Hydrolysis Catalysed by Lipase LKT400XL with Isooctane as the Organic Solvent Experiments 35 to 39 were conducted as described in 2.5, except that different amount of deionized water was added (corresponding to the amount of 25%, 75%, 100%, 150% and 200% of the oil weight (including water present in the enzyme solution)), and 10 mL of isooctane as the organic solvent (the ratio of "the volume of organic solvent in mL to the weight of oil in gram (V/W)" was 200%) was added. After the completion of the reaction, the acid value and hydrolysis rate were calculated as shown in Table 7.

TABLE 7

Different amount of water for the hydrolysis by LKT400XL with isooctane

| Exp. No. | 35 | 32 | 36 | 37 | 38 | 39 |
|---|---|---|---|---|---|---|
| Isooctane | | | 10 mL | | | |
| Water, mL | 1.25 (25%) | 2.5 (50%) | 3.75 (75%) | 5 (100%) | 7.5 (150%) | 10 (200%) |
| Temp. | | | 45° C. | | | |
| LKT400XL | | | 2% (V/W) of HCO | | | |
| AV (72 h) | 177.68 | 178.42 | 177.23 | 181.50 | 180.11 | 179.63 |
| Hydrolysis rate (%) | 94.01 | 94.41 | 93.77 | 96.05 | 95.31 | 95.05 |

When the ratio of isooctane volume in mL to the HCO weight in gram was 200% and the amount of LKT400XL added was 2%, different amounts of water all ended in final products with acid values higher than 175. Preferably, water amount in the range of 20%-200% of the weight of HCO was used.

2.7 the Effect of Temperature on the Hydrolysis Catalysed by Lipase LKT400XL with Isooctane as the Organic Solvent Experiments 40 to 43 were conducted as described in 2.5, except that 5 mL of deionized water and 10 mL of isooctane were added. The hydrolysis reactions were undergone at different temperature (37° C., 40° C., 50° C. and 55° C.). After the completion of the reaction, the acid value and hydrolysis rate were calculated as shown in Table 8.

TABLE 8

Different temperatures for the hydrolysis of HCO by LKT400XL with isooctane

| Exp. No. | 40 | 41 | 37 | 42 | 43 |
|---|---|---|---|---|---|
| HCO powder | | | 5 g | | |
| Isooctane | | | 10 mL | | |
| water | | | 5 mL | | |
| LKT400XL | | | 2% (V/W) of HCO | | |
| Temp. (° C.) | 37 | 40 | 45 | 50 | 55 |
| AV (72 h) | 158.77 | 152.99 | 181.50 | 180.93 | 179.27 |
| Hydrolysis rate (%) | 83.95 | 80.87 | 96.05 | 95.74 | 94.86 |

The reaction can be conducted between 37° C.-55° C. When the reaction was conducted under a temperature of higher than 40° C., final product with higher acid value was obtained. Especially when the temperature was between 45° C. and 55° C., acid values around 180 were obtained.

2.8 the Effect of Enzyme Dosage on the Hydrolysis Catalysed by Lipase LKT400XL with Isooctane as the Organic Solvent Experiments 44 to 50 were conducted as described in 2.7, except that different amount of Lipase LKT400XL (50 μL, 40 μL, 25 μL or 15 μL corresponding to 1%, 0.8%, 0.5% or 0.3% of HCO) was added and the reaction was conducted at a temperature of 45° C. or 50° C. After the completion of the reaction, the acid values were determined and hydrolysis rates were calculated and shown in Table 9 and Table 10.

TABLE 9

Different dosages of LKT400XL for the hydrolysis with isooctane at 45° C.

| Exp. No. | 37 | 44 | 45 | 46 | 47 |
|---|---|---|---|---|---|
| HCO powder | | | 5 g | | |
| Isooctane | | | 10 mL | | |
| water | | | 5 mL | | |

TABLE 9-continued

Different dosages of LKT400XL for the hydrolysis
with isooctane at 45° C.

| Exp. No. | 37 | 44 | 45 | 46 | 47 |
|---|---|---|---|---|---|
| Temp. | | | 45° C. | | |
| LKT400XL | 2% | 1% | 0.8% | 0.5% | 0.3% |
| AV (72 h) | 181.50 | 175.92 | 137.14 | 93.02 | 92.32 |
| Hydrolysis rate (%) | 96.05 | 93.08 | 72.44 | 48.95 | 48.58 |

TABLE 10

Different dosages of LKT400XL for the hydrolysis
with isooctane at 50° C.

| Exp. No. | 42 | 48 | 49 | 50 |
|---|---|---|---|---|
| HCO powder | | 5 g | | |
| Isooctane | | 10 mL | | |
| Water | | 5 mL | | |
| Temp. | | 50° C. | | |
| LKT400XL | 2% | 0.8% | 0.5% | 0.3% |
| AV (72 h) | 180.93 | 170.58 | 150.31 | 115.39 |
| Hydrolysis rate (%) | 95.74 | 90.23 | 79.45 | 60.86 |

When the amount of enzyme used was not less than 1%, reaction product with acid values of higher than 170 could be obtained. LKT400XL has better catalyzing activity under 50° C., and reaction product with acid values of higher than 170 could be obtained with 0.8% of enzyme.

Example 3—EVERSA Catalysed HCO Hydrolysis 3.1 the Effect of Different Organic Solvents on the Hydrolysis 5 grams of HCO in the form of fine powder was put into the reactor, then 5 mL (including the water present in the enzyme solution) of deionized water (100% of the weight of oil) was added, and 25 mL of organic solvent (the ratio of "the volume of organic solvent in mL to the weight of oil in gram (V/W)" was 500%) was added into the reactor. Then 100 μL of EVERSA (2% (V/W) of HCO) was added into the mixture. The mixture was heated to the reaction temperature of 37° C. while stirring at 450 rpm. The stirring was continued through the reaction, and the reaction was stopped after 24 hours for analysis. The acid values of the hydrolysis products were determined and the hydrolysis rates were calculated and shown in Table 11.

TABLE 11

Comparison of different organic solvents for
the hydrolysis of HCO

| Exp. No | Organic solvent | AV (24 h) | Hydrolysis rate, % |
|---|---|---|---|
| 51 | acetone | 35.88 | 18.54 |
| 52 | acetonitrile | 42.10 | 21.85 |
| 53 | N,N-dimethylformamide (DMF) | 44.88 | 23.33 |
| 54 | tert-butanol (t-BuOH) | 74.05 | 38.86 |
| 55 | diethyl ether | 129.03 | 68.12 |
| 56 | MTBE | 130.52 | 68.91 |
| 57 | n-hexane | 126.82 | 66.94 |
| 58 | cyclohexane | 133.24 | 70.39 |
| 59 | n-heptane | 135.15 | 71.38 |
| 60 | isooctane | 171.23 | 90.58 |

Non-polar solvent generally has better effects on obtaining final products with higher acid values. t-BuOH was better than other polar solvent. With optimization of reaction conditions, steric alcohol like t-butanol, non-polar solvent used alone or mixed with each other was potentially possible for achieving high acid value.

3.2 MTBE as Solvent for EVERSA Catalysed HCO Hydrolysis 3.2.1 the Effect of MTBE Amount on the Hydrolysis Catalysed by EVERSA 5 grams of HCO in the form of fine powder was put into a reactor, then 5 mL of deionized water were added to the reactor to the amount of 100% of the oil weight (including water present in the enzyme solution), and different volume (5 mL, 10 mL, 15 mL or 25 mL) of MTBE as organic solvent (the ratio of "the volume of organic solvent in mL to the weight of oil in gram (V/W)" was 100%, 200%, 300% or 500%) was added into the reactor. Then 50 μL of EVERSA (1% (V/W) of HCO) was added into the mixture. The mixture was heated with a stirring rate of 450 rpm to the reaction temperature of 45° C. The stirring was continued through the reaction, and the hydrolysis reactions were monitored at 48 h. After the completion of the reaction, acid values were determined and the hydrolysis rates were calculated and shown in Table 12 below.

TABLE 12

Different amount of MTBE for the hydrolysis of HCO by Eversa

| Exp. No. | 61 | 62 | 63 | 64 |
|---|---|---|---|---|
| HCO powder | | 5 g | | |
| MTBE (% (V/W) of HCO) | 5 mL (100%) | 10 mL (200%) | 15 mL (300%) | 25 mL (500%) |
| Water | | 5 mL, 100% (V/W) of HCO | | |
| Eversa | | 50 μL, 1% (V/W) of HCO | | |
| Temp. | | 45° C. | | |
| AV (28 h) | 166.84 | 156.57 | 149.84 | 156.13 |
| AV (48 h) | 161.26 | 164.57 | 161.74 | 153.51 |
| Hydrolysis rate at 48 h (%) | 85.27 | 87.03 | 85.53 | 81.15 |

When 100% to 300% of MTBE was used, the acid values of the reaction products were higher than 160 after 48 h reaction.

3.2.2 the Effect of Water Amount on the Hydrolysis Catalysed by EVERSA with MTBE as the Organic Solvent.

Experiments 65 to 71 were conducted as described in 3.2.1, except that different amount of deionized water was added, and 10 mL of MTBE was added (the ratio of "the volume of organic solvent in mL to the weight of oil in gram (V/W)" was 200%). The reaction temperature was 50° C. After the completion of the reaction at 72 h, the acid values were determined and hydrolysis rates were calculated as shown in Table 13. Experiments 72 to 75 were similarly conducted, but for 48 h under a temperature of 45° C., and with 10 mL (200% (V/W) of HCO) of MTBE. The AV and hydrolysis rates are shown in Table 14.

TABLE 13

Different amount of deionized water for the hydrolysis of HCO
by Eversa with MTBE as the organic solvent

| Exp. No. | 65 | 66 | 67 | 68 | 69 | 70 | 71 |
|---|---|---|---|---|---|---|---|
| HCO powder | 5 g | | | | | | |
| MTBE | 10 mL, 200% (V/W) of HCO | | | | | | |
| Water | 25% | 50% | 75% | 100% | 150% | 200% | 300% |
| Eversa | 50 μL, 1% (V/W) of HCO | | | | | | |
| Temp. | 50° C. | | | | | | |
| AV (72 h) | 161.92 | 168.73 | 166.85 | 173.30 | 174.56 | 178.43 | 175.18 |
| Hydrolysis rate, (%) | 85.62 | 89.25 | 88.25 | 91.69 | 92.35 | 94.41 | 92.68 |

TABLE 14

Different amount of deionized water for the hydrolysis of HCO
by Eversa with MTBE as the organic solvent

| Exp. No. | 72 | 73 | 62 | 74 | 75 |
|---|---|---|---|---|---|
| HCO | 5 g | | | | |
| MTBE | 10 mL, 200% (V/W) of HCO | | | | |
| Water | 25% | 50% | 100% | 150% | 200% |
| Eversa | 50 μL, 1% (V/W) of HCO | | | | |
| Temp. | 45° C. | | | | |
| AV (48 h) | 149.18 | 151.19 | 164.57 | 163.4 | 171.89 |
| Hydrolysis rate, % | 78.84 | 79.91 | 87.04 | 86.01 | 90.93 | the oil weight (including water present in the enzyme solution), and 30 mL of n-hexane as organic solvent (the ratio of "the volume of organic solvent in mL to the weight of oil in gram (V/W)" was 300%) was added into the reactor. Then 50 μL of EVERSA (0.5% (V/W) of HCO) was added into the mixture. The mixture was heated with a stirring rate of 450 rpm to the reaction temperature of 50° C. The stirring was continued through the reaction. After 72 h, the acid values were determined and hydrolysis rates were calculated. Details are shown in Table 15.

TABLE 15

Different amount of water on the hydrolysis by Eversa
with n-hexane as organic solvent

| Exp. No. | 76 | 77 | 78 | 79 | 80 | 81 | 82 | 83 |
|---|---|---|---|---|---|---|---|---|
| HCO powder | 10 g | | | | | | | |
| Eversa, μL (% (V/W) of HCO) | 50 (0.5%) | | | | | | | 100 (1%) |
| H$_2$O, mL (% (V/W) of HCO) | 1.5 (15%) | 2.5 (25%) | 5.0 (50%) | 7.5 (75%) | 10 (100%) | 15 (150%) | 20 (200%) | 1.5 (15%) |
| n-Hexane, mL (% (V/W) of HCO) | 30 (300%) | | | | | | | 20 (200%) |
| AV (72 h) | 92.03 | 142.49 | 172.06 | 180.23 | 179.10 | 107.03 | 110.74 | 175.10 |
| Hydrolysis rate, % | 48.43 | 75.28 | 91.02 | 95.37 | 94.77 | 56.41 | 58.39 | 92.64 |

When 200% of MTBE was used in the hydrolysis of HCO by EVERSA, by adjusting water amount, acid values of higher than 165 could be easily achieved under 50° C. with water amount in a wide range.

When 200% of MTBE was used in the hydrolysis of HCO by EVERSA under 45° C., by using water amount in a range of not less than 100%, acid values higher than 160 could be achieved. Especially when water amount is in a range around 200%, acid values of higher than 170 was obtained.

3.3 n-Hexane as Solvent for EVERSA Catalysed HCO Hydrolysis.

3.3.1 the Effect of Water Amount on the Hydrolysis Catalysed by EVERSA with n-Hexane as the Organic Solvent 10 grams of HCO in the form of fine powder was put into a reactor, then deionized water were added to the reactor to the amount of 15%, 25%, 50%, 75%, 100%, 150%, 200% of When the water amount was higher than 25% and lower than 150%, acid values for the hydrolysis products obtained were higher. Especially when water amount was in the range of from 50% to 100%, acid values were higher than 170, corresponding to hydrolysis rate of higher than 89.92%.

However, if the amount of EVERSA was increased to 1% (Exp. No. 83), even under a water amount of 15% and a n-hexane amount of 200%, acid value of higher than 175 was obtained.

3.3.2 the Effect of n-Hexane Amount on the Hydrolysis Catalysed by EVERSA

Experiments 84 to 87 were conducted as described in 3.3.1, except that 7.5 mL of deionized water were added, and 10, 20, 40 or 50 mL of n-hexane as the solely organic solvent (the ratio of "the volume of organic solvent in mL to the weight of oil in gram (V/W)" was 100%, 200%, 400% or 500%) was added. After the completion of the reaction, the acid values were determined and hydrolysis rates were calculated, and results are shown in Table 16.

TABLE 16

Different amount of n-hexane on the hydrolysis of HCO by Eversa

| Exp. No. | 84 | 85 | 79 | 86 | 87 |
|---|---|---|---|---|---|
| HCO, g | | | 10 | | |
| H$_2$O, mL (% (V/W) of HCO) | | | 7.5 (75%) | | |
| n-Hexane, mL (% (W/W) of HCO) | 10 (100%) | 20 (200%) | 30 (300%) | 40 (400%) | 50 (500%) |
| AV (72 h) | 172.23 | 165.68 | 180.23 | 180.63 | 168.88 |
| Hydrolysis rate, % | 91.11 | 87.63 | 95.37 | 95.58 | 89.33 |

When water was used with the amount of 75% of the weight of HCO, acid value of final products could achieve higher than 165 easily. The data in the table shows n-hexane amount in the range of from 200% to 500% (V/W) of HCO could help achieve acid values higher than 170, or even around 180, especially when n-hexane amount was in the range of from 300% to 400%.

3.3.3 the Effect of EVERSA Dosage on the Hydrolysis Catalysed by EVERSA with n-Hexane as the Organic Solvent.

Experiments 88 to 94 were conducted as described in 3.3.1, except that 7.5 mL of deionized water, 10, 20 or 30 mL of n-hexane as the solely organic solvent, and different amount of EVERSA (100 μL, 50 μL or 30 μL corresponding to 1%, 0.5% or 0.3% (V/W) of HCO) were added. Results are shown in Table 17.

TABLE 17

Different dosages of Eversa on the hydrolysis of HCO with n-hexane as solvent

| Exp. No. | 88 | 84 | 89 | 90 | 91 | 92 | 93 | 79 | 94 |
|---|---|---|---|---|---|---|---|---|---|
| HCO, g | | | | | 10 | | | | 50 |
| H2O, mL (% of HCO) | | | | | 7.5 (75%) | | | | 37.5 (75%) |
| n-Hexane, mL | 10 | 10 | 10 | 20 | 20 | 20 | 30 | 30 | 100 (200%) |
| Eversa, μL (% of HCO) | 100 (1%) | 50 (0.5%) | 30 (0.3%) | 100 (1%) | 50 (0.5%) | 30 (0.3%) | 100 (1%) | 50 (0.5%) | 150 (0.3%) |
| AV (72 h) | 180.53 | 172.23 | 177.22 | 180.62 | 165.68 | 177.73 | 181.33 | 180.23 | 165.25 |
| Hydrolysis rate, % | 95.53 | 91.11 | 93.77 | 95.58 | 87.63 | 94.04 | 95.96 | 95.37 | 87.40 |

When 100% n-hexane and 75% water were used, acid value can easily reach 170 or higher by using EVERSA in the amount of from 0.3% to 1%. When 200% n-hexane was used, acid values were easily achieved higher than 165. When 300% n-hexane was added, EVERSA in higher amount of >0.5% could help achieve acid values around 180. Overall 1% EVERSA could guarantee acid value of the hydrolysis product to be around 180. Even using EVERSA in an amount of <1% under mild reaction conditions could achieve acid value higher than 170, or near 180.

3.3.4 the Effect of Temperature on the Hydrolysis Catalysed by EVERSA with n-Hexane as the Organic Solvent Experiments 95 to 98 were conducted as described in 3.3.1, except that 7.5 mL of deionized water and 30 mL of n-hexane as organic solvent were added. The hydrolysis reactions were undergone at different temperature (37° C., 40° C., 45° C. and 55° C.) while stirring at 450 rpm. After the completion of the reaction, the acid values were determined and hydrolysis rates were calculated. Results are shown in Table 18.

TABLE 18

The effect of temperature on the hydrolysis by Eversa with n-hexane as solvent

| Exp. No. | 95 | 96 | 97 | 94 | 98 |
|---|---|---|---|---|---|
| HCO powder | | | 1 g | | |
| n-Hexane | | | 30 mL | | |
| water | | | 7.5 mL | | |
| Eversa | | | 0.5% (V/W) of HCO | | |
| Temp. (° C.) | 37 | 40 | 45 | 50 | 55 |
| AV (72 h) | 118.59 | 150.81 | 152.68 | 180.23 | 160.52 |
| Hydrolysis rate (%) | 62.56 | 79.71 | 80.71 | 95.37 | 84.88 |

When the hydrolysis was carried out under a temperature between 40° C. and 55° C., higher acid values were obtained. Hydrolysis at a temperature of 50° C. seems to be the most optimized one.

3.4 Isooctane as Solvent for EVERSA Catalysed HCO Hydrolysis.

3.4.1 the Effect of Water Amount on the Hydrolysis Catalysed by EVERSA with Isooctane as Solvent.

10 grams of HCO in the form of fine powder was put into a reactor, then deionized water were added to the reactor with the amount of 25%, 50%, 100%, 150%, 200% of the oil weight (including water present in the enzyme solution), and 30 mL of isooctane as organic solvent (the ratio of "the volume of organic solvent in mL to the weight of oil in gram (V/W)" was 300%) was added into the reactor. Then 100 μL of EVERSA (1% (V/W) of HCO) was added into the mixture. The mixture was heated with a stirring rate of 450 rpm to the reaction temperature of 50° C. The stirring was continued through the reaction, and the hydrolysis reactions were monitored at 72 h. After the completion of the reaction, the acid values were determined and the hydrolysis rates were calculated. Results are shown in Table 19.

TABLE 19

Different amount of water for hydrolysis by Eversa with isooctane

| Exp. No. | 99 | 100 | 101 | 102 | 103 |
|---|---|---|---|---|---|
| HCO powder | | | 10 g | | |
| H$_2$O, mL (% of HCO) | 2.5 (25%) | 5.0 (50%) | 10 (100%) | 15 (150%) | 20 (200%) |
| Isooctane | | | 30 mL | | |

TABLE 19-continued

Different amount of water for hydrolysis by Eversa with isooctane

| Exp. No. | 99 | 100 | 101 | 102 | 103 |
|---|---|---|---|---|---|
| Eversa | | 100 µL (1% of HCO) | | | |
| AV (72 h) | 161.44 | 166.33 | 177.08 | 177.12 | 169.46 |
| Hydrolysis rate (%) | 85.37 | 87.97 | 93.69 | 93.71 | 89.64 |

When isooctane is used as the organic solvent, water amount in the range of higher than 25% could help achieve acid values higher than 160, preferably from 50% to 200% could help achieve acid value higher than 165, more preferably from 50% to 200%, even more preferably from 100% to 200%, most preferably from 100% to 150%.

3.4.2 the Effect of Isooctane Amount on the Hydrolysis Catalysed by EVERSA

Experiments 104 to 106 were conducted as described in 3.4.1, except that 15 mL of deionized water, and different amount of isooctane (the ratio of "the volume of organic solvent in mL to the weight of oil in gram (V/W)" was 100%, 200%, or 500%) were added. After the completion of the reaction, the acid values were determined and the hydrolysis rates were calculated. Results are shown in the Table 20.

TABLE 20

Different amount of isooctane for the hydrolysis by Eversa

| Exp. No. | 104 | 105 | 102 | 106 |
|---|---|---|---|---|
| HCO, g | | 10 | | |
| H$_2$O, mL | | 15 | | |
| Eversa | | 100 µL (1% (V/W) of HCO) | | |
| Isooctane, mL (% of HCO) | 10 (100%) | 20 (200%) | 30 (300%) | 50 (500%) |
| AV (72 h) | 179.35 | 175.58 | 177.12 | 184.95 |
| Hydrolysis rate (%) | 94.90 | 92.89 | 93.71 | 97.88 |

Different amount of isooctane can easily help acid values of the reaction products reach higher than 175, especially when from 100% to 500% of isooctane is used. Most preferably, 500% isooctane was used to obtain acid value around 185.

3.4.3 the Effect of EVERSA Dosage on the Hydrolysis with Isooctane as the Organic Solvent Experiments 107 to 109 were conducted as described in 3.4.1, except that 15 mL of deionized water, 30 mL of isooctane, and different amount of EVERSA (50 UL, 30 µL or 20 µL corresponding to 0.5%, 0.3% or 0.2% (V/W) of HCO) were added. After the completion of the reaction, the acid values were determined and the hydrolysis rates were calculated. Results are shown in Table 21.

TABLE 21

Different dosage of Eversa on the HCO hydrolysis with isooctane

| Exp. No. | 102 | 107 | 108 | 109 |
|---|---|---|---|---|
| HCO powder, g | | 10 | | |
| H$_2$O, mL (% of HCO) | | 15 (150%) | | |
| Isooctane | | 30 mL (300% of HCO) | | |
| Temp. | | 50° C. | | |
| Eversa, µL (% of HCO) | 100 (1%) | 50 (0.5%) | 30 (0.3%) | 20 (0.2%) |
| AV (72 h) | 181.12 | 178.76 | 160.13 | 150.03 |
| Hydrolysis rate (%) | 95.84 | 94.59 | 84.67 | 79.30 |

EVERSA dosage higher than 0.3% could help obtain reaction products with acid values higher than 160, especially EVERSA dosage of 0.5% to 1% could get acid values higher than 175. Higher amount of EVERSA dosage will help obtain acid values no less than Exp. 102 and 107.

3.5 Tert-Butanol as Solvent for EVERSA Catalysed HCO Hydrolysis.

3.5.1 the Effect of Water Amount on the Hydrolysis Catalysed by EVERSA with t-BuOH as Organic Solvent.

5 grams of HCO in the form of fine powder was put into a reactor, then different amount of deionized water was added to the amount of from 25% to 500% (V/W) of the oil weight (including water present in the enzyme solution), and 5 mL of t-BuOH (the ratio of "the volume of organic solvent in mL to the weight of oil in gram (V/W)" was 100%) were added into the reactor. Then 50 µL EVERSA (1% (V/W) of HCO) was added into the mixture. The mixture was heated with a stirring rate of 450 rpm to the reaction temperature of 50° C. The stirring was continued through the reaction, and the reaction lasted for 72 hours. After the completion of the reaction, the acid values were determined and the hydrolysis rates were calculated. Results are shown in Table 22 below.

TABLE 22

Different amount of water for hydrolysis by Eversa with t-BuOH

| Exp. No. | 110 | 111 | 112 | 113 | 114 | 115 | 116 | 117 | 118 |
|---|---|---|---|---|---|---|---|---|---|
| HCO powder, g | | | | | 5 | | | | |
| H$_2$O, mL (% of HCO) | 1.25 (25%) | 2.5 (50%) | 3.75 (75%) | 5 (100%) | 7.5 (150%) | 10 (200%) | 15 (300%) | 20 (400%) | 25 (500%) |
| t-BuOH, mL (% (V/W) of HCO) | | | | | 5 (100%) | | | | |
| Eversa | | | | | 1% | | | | |
| AV (72 h) | 76.67 | 125.14 | 124.17 | 157.42 | 127.77 | 140.84 | 153.74 | 154.97 | 157.19 |
| Hydrolysis rate, % | 40.25 | 66.05 | 65.53 | 83.23 | 67.45 | 74.41 | 81.27 | 81.93 | 83.11 |

3.5.2 the Effect of t-BuOH Amount on the Hydrolysis Catalysed by EVERSA

Experiments 119 to 121 were conducted as described in 3.5.1, except that 5 mL of deionized water, and different amount of t-BuOH (the ratio of "the volume of organic solvent in mL to the weight of oil in gram (V/W)" was 200%, 300%, or 500%) were added. After the completion of the reaction, the acid values were determined and the hydrolysis rates were calculated. Results are shown in Table 23.

TABLE 23

Different amount of t-BuOH for hydrolysis by Eversa

| Exp. No. | 113 | 119 | 120 | 121 |
|---|---|---|---|---|
| HCO powder, g | 5 | | | |
| H$_2$O, mL (% of HCO) | 5 (100%) | | | |
| t-BuOH, mL (% (V/W) of HCO) | 5 (100%) | 10 (200%) | 15 (300%) | 25 (500%) |
| Eversa | 1% | | | |
| AV (72 h) | 157.42 | 36.69 | 46.04 | 117.28 |
| Hydrolysis rate, % | 83.33 | 18.97 | 23.95 | 61.87 |
| Time, h | 72 | | | |

3.6 Mixture of Organic Solvents for EVERSA Catalysed HCO Hydrolysis.

3.6.1 Acetone/n-Hexane Mixture as Organic Solvent for Hydrolysis Catalysed by EVERSA.

10 grams of HCO in fine powder form was put in the reactor, then 25 mL of deionized water was added. 15 mL of acetone and n-hexane mixture in different ratio was added as shown in the Table 24. 30 µL of EVERSA (0.3% (V/W) of HCO) or 50 µL of EVERSA (0.5% (V/W) of HCO) was then added to the reactor. The mixture was heated with a stirring rate of 450 rpm to the reaction temperature of 50° C. The stirring was continued through the reaction, and the reaction continues 72 hours. After the completion of the reaction, the acid values were determined and the hydrolysis rates were calculated. Results are shown in Table 24.

TABLE 24

Acetone/n-hexane mixture for the hydrolysis by Eversa

| Exp. No. | 122 | 123 | 124 | 125 | 126 | 127 |
|---|---|---|---|---|---|---|
| Eversa (% (V/W) of HCO) | | | 0.5% | | | 0.3% |
| HCO powder (g) | | | 10 | | | |
| Acetone/n-hexane, mL (V:V) | 0/15 (0:100) | 3/12 (20:80) | 4.5/10.5 (30:70) | 6/9 (40:60) | 7.5/7.5 (50:50) | 6/9 (40:60) |
| H$_2$O | | | 25 mL (250%) | | | 15 mL (150%) |
| AV (72 h) | 181.28 | 169.47 | 165.25 | 163.02 | 164.48 | 159.78 |
| Hydrolysis rate, % | 95.93 | 89.64 | 87.40 | 86.21 | 86.99 | 84.49 |
| Time | | | 72 h | | | |
| Temp. (° C.) | | | 50° C. | | | 50° C. (24 h) + 45° C. (48 h) |

Table 24 shows by adding the mixture of acetone/n-hexane as the organic solvent, the maximal AV achieved with 0.3-0.5% EVERSA is near 170, and AV can easily reach 160 and 165 under optimized reaction conditions.

3.6.2 t-BuOH/n-Hexane Mixture as the Organic Solvent for Hydrolysis Catalysed by EVERSA.

3.6.2.1 the Effect of Mixing Ratio and Solvent Amount on the Hydrolysis Catalysed by EVERSA with t-BuOH/n-Hexane.

10 grams of HCO in fine powder form was put in the reactor, then 15 mL of t-BuOH/n-hexane mixture with different volume to volume ratio (t-BuOH:n-hexane 25:75, 30:70 or 35:75) was added to the reactor. 15 mL of deionized water (150% weight of HCO) was then added. 30 µL of EVERSA (0.3% (V/W) of HCO) was added. The mixture was heated with a stirring rate of 450 rpm to the reaction temperature of 50° C. The stirring was continued through the reaction, and the reaction was undertaken at 50° C. for 66 hours. After the completion of the reaction, the acid values were determined and hydrolysis rates were calculated. Results are shown in Table 25.

TABLE 25 t-BuOH/n-hexane mixture in different ratios for the hydrolysis by Eversa

| Exp. No. | 128 | 129 | 130 |
|---|---|---|---|
| HCO powder | | 10 g | |
| t-BuOH:n-hexane ratio | 25:75 | 30:70 | 35:65 |
| t-BuOH, mL | 3.75 | 4.5 | 5.25 |
| n-Hexane, mL | 11.25 | 10.5 | 9.75 |
| Water | | 15 mL | |
| Eversa | | 0.3% (V/W) of HCO | |
| Temp. | | 50° C. | |
| AV (66 h) | 152.17 | 166.69 | 155.23 |
| Hydrolysis rate, % | 84.44 | 88.16 | 82.06 |

By optimizing mixing ratio, t-BuOH/n-hexane mixture could be used as organic solvent for achieving AV higher than 165 in the hydrolysis of HCO catalyzed by 0.3% of EVERSA.

3.6.2.2 the Effect of Water Amount to the EVERSA Catalyzed Hydrolysis with t-BuOH/n-Hexane as Organic Solvent.

Experiments 131 to 135 were conducted as described in 3.6.2.1, except that 15 mL of t-BuOH/n-hexane mixture with volume to volume ratio of 30:70 was added to the reactor, and different amount of deionized water (7.5 mL, 10 mL, 20 mL, 25 mL or 30 mL corresponding to 75%, 100%, 200%, 250% or 300% of the weight of HCO, respectively) was then added. After the completion of the reaction, the acid values were determined and the hydrolysis rates were calculated. Results are shown in Table 26.

TABLE 26

Different amount of water for the hydrolysis by Eversa with t-BuOH/n-hexane mixture

| Exp. No. | 131 | 132 | 129 | 133 | 134 | 135 |
|---|---|---|---|---|---|---|
| HCO powder | | | 10 g | | | |
| t-BuOH | | | 4.5 mL | | | |
| n-Hexane | | | 10.5 mL | | | |
| Water | 7.5 mL | 10 mL | 15 mL | 20 mL | 25 mL | 30 mL |
| Eversa | | | 0.3% (V/W) of HCO | | | |
| Temp. | | | 50° C. | | | |
| AV (66 h) | 161.02 | 157.17 | 166.69 | 173.28 | 177.52 | 162.40 |
| Hydrolysis rate, % | 85.15 | 83.10 | 88.16 | 91.67 | 93.93 | 85.88 |

When t-BuOH/n-hexane mixture is used as organic solvent, water amount in the range of more than 100% and less than 500% could help achieve acid values of higher than 160; and water amount in the range of from 150% to 300% could help achieve acid values of higher than 165. Under optimized conditions, acid values could reach higher than 170.

3.6.2.3 the Effect of EVERSA Dosage to the Hydrolysis of HCO with t-BuOH/n-Hexane (3:7) Mixture as the Organic Solvent.

Experiments 136 to 138 were conducted as described in 3.6.2.2, except that 10 mL of deionized water and different EVERSA dosage was added as shown in Table 27. After the completion of the reaction at 72 h, the acid values were determined and the hydrolysis rates were calculated. Results are shown in Table 27.

TABLE 27

Eversa dosages for the hydrolysis with t-BuOH/n-hexane mixture

| Exp. No. | 136 | 137 | 134 | 138 |
|---|---|---|---|---|
| HCO powder, g | | 10 | | |
| H₂O, mL (% of HCO) | | 25 (250%) | | |
| t-BuOH/n-hexane (3:7) | | 15 mL (150% (V/W) of HCO) | | |
| Temp. | | 50° C. | | |
| Eversa (% of HCO) | 100 μL (1%) | 50 μL (0.5%) | 30 μL (0.3%) | 20 μL (0.2%) |
| AV | 178.99 (72 h) | 176.44 (72 h) | 177.52 (66 h) | 165.68 (72 h) |
| Hydrolysis rate, % | 94.71 | 93.35 | 93.93 | 87.79 |

3.6.2.4 the Effect of Temperature to the EVERSA Hydrolysis of HCO with t-BuOH/n-Hexane (3:7) Mixture as the Organic Solvent.

Experiments 139 to 142 were conducted as described in 3.6.2.2, except that 10 mL of deionized water was added, and reaction was conducted under different temperature as shown in Table 28. After the completion of the reaction at 72 h, the acid values were determined and the hydrolysis rates were calculated.

TABLE 28

Different temperature for the hydrolysis by Eversa with t-BuOH/n-hexane mixture

| Exp. No. | 139 | 140 | 141 | 134 | 142 |
|---|---|---|---|---|---|
| HCO powder, g | | | 10 | | |
| H₂O, mL (% of HCO) | | | 25 (250%) | | |
| t-BuOH/n-hexane (3:7) | | | 15 mL (150% (V/W) of HCO) | | |
| Eversa (% of HCO) | | | 30 μL (0.3%) | | |
| Temp.° C. | 37 | 40 | 45 | 50 | 55 |
| AV | 95.47 (72 h) | 104.91 (72 h) | 114.65 (72 h) | 177.52 (66 h) | 176.94 (72 h) |
| Hydrolysis rate, % | 50.79 | 55.28 | 60.47 | 93.93 | 93.62 |

3.6.3 t-BuOH/Isooctane Mixture as Organic Solvent for Hydrolysis Catalysed by EVERSA.

3.6.3.1 the Amount of t-BuOH/Isooctane (3:7) Mixture for EVERSA Catalysed Hydrolysis of HCO.

10 grams of HCO in fine powder form was put in the reactor, then different volume of t-BuOH/n-hexane mixture with V/V ratio of 3:7 was added to the reactor. 25 mL of deionized water (150% weight of HCO) was then added. 30 μL of EVERSA (0.3% (V/W) of HCO) was added. The mixture was heated with a stirring rate of 450 rpm to the reaction temperature of 50° C. The stirring was continued through the reaction, and the reaction was undertaken at 50° C. for 72 hours. After the completion of the reaction, the acid values were determined and the hydrolysis rates were calculated. Results are shown in Table 29.

TABLE 29

Different amount of t-BuOH/isooctane mixture (3:7) for the hydrolysis by Eversa

| Exp. No. | 143 | 144 | 145 | 146 | 147 |
|---|---|---|---|---|---|
| HCO powder (g) | | | 10 | | |
| H₂O | | | 25 mL (250%) | | |
| Eversa | | | 0.3% (V/W) of HCO | | |
| t-BuOH/isooctane (3:7) (mL) | 7.5 mL | 10 mL | 15 mL | 20 mL | 25 mL |
| AV (72 h) | 168.28 | 163.03 | 173.03 | 164.61 | 162.40 |
| Hydrolysis rate, % | 89.01 | 86.22 | 91.54 | 87.06 | 85.88 |
| Temp. | | | 50° C. | | |

3.6.3.2 the Water Amount for EVERSA Catalysed Hydrolysis of HCO with t-BuOH/Isooctane (3:7) Mixture as the Organic Solvent.

Experiments 148 to 150 were conducted as described in 3.6.3.1, except that 15 mL of t-BuOH/isooctane mixture (3:7) was added to the reactor, and different amount of deionized water (15 mL, 20 mL, or 30 mL corresponding to 150%, 200%, or 300% V/W of the weight of HCO, respectively) was then added, as shown below in Table 30. After the completion of the reaction at 72 h, the acid values were determined and the hydrolysis rates were calculated.

TABLE 30

Different amount of water for the hydrolysis by Eversa with t-BuOH/isooctane mixture

| Exp. No. | 148 | 149 | 145 | 150 |
|---|---|---|---|---|
| HCO powder (g) | | | 10 | |
| t-BuOH/isooctane (3:7) (mL) | | | 15 mL | |
| Eversa | | | 0.3% (V/W) of HCO | |
| H₂O | 15 mL | 20 mL | 25 mL | 30 mL |
| AV (72 h) | 162.54 | 165.87 | 173.03 | 169.37 |
| Hydrolysis rate, % | 85.95 | 87.73 | 91.54 | 89.59 |
| Temp. | | | 50° C. | |

3.6.3.3 the Effect of EVERSA Dosage on the Hydrolysis of HCO with t-BuOH/Isooctane (3:7) Mixture as the Organic Solvent.

Experiments 151 and 152 were conducted as described in 3.6.3.2, except that 25 mL of deionized water and different dosages of EVERSA were added as shown below in Table 31. After the completion of the reaction after 72 h, the acid values were determined and the hydrolysis rates were calculated.

TABLE 31

Eversa dosages for the hydrolysis with t-BuOH/isooctane mixture

| Exp. No. | 151 | 145 | 152 |
|---|---|---|---|
| HCO powder, g | | 10 | |
| H$_2$O, mL (% of HCO) | | 25 (250%) | |
| t-BuOH/isooctane (3:7) | | 15 mL (150% (V/W) of HCO) | |
| Temp. | | 50° C. | |
| Eversa (V/W % of HCO) | 100 µL (1%) | 30 µL (0.3%) | 20 µL (0.2%) |
| AV (72 h) | 174.18 | 173.03 | 146.31 |
| Hydrolysis rate, % | 92.15 | 91.54 | 77.32 |

Example 4—TLL-SH Catalysed HCO Hydrolysis

4.1 the Effect of Water Amount to the TLL-SH Catalysed HCO Hydrolysis with n-Hexane as Organic Solvent 10 grams of HCO in fine powder form was put in the reactor, then 30 mL of n-hexane was added to the reactor. Different amount of deionized water (2.5 mL, 5 mL, 7.5 mL, 10 mL, mL, 20 mL, 30 mL or 40 mL corresponding to 25%, 50%, 75%, 100%, 150%, 200%, 300% or 400% of the weight of HCO, respectively) was then added. 100 µL (1% (V/W) of HCO) of TLL-SH was added. The mixture was heated with a stirring rate of 450 rpm to the reaction temperature of 50° C. The stirring was continued through the reaction, and the reaction was undertaken at 50° C. for 72 hours. After the completion of the reaction, the acid values were determined and the hydrolysis rates were calculated. Results are shown in Table 32.

TABLE 32

Different amount of water for the hydrolysis by TLL-SH with n-hexane

| Exp. No. | 153 | 154 | 155 | 156 | 157 | 158 | 159 | 160 |
|---|---|---|---|---|---|---|---|---|
| HCO powder, g | | | | 10 | | | | |
| H$_2$O, mL (% of HCO) | 2.5 (25%) | 5 (50%) | 7.5 (75%) | 10 (100%) | 15 (150%) | 20 (200%) | 30 (300%) | 40 (400%) |
| n-Hexane, mL (% (V/W) of HCO) | | | | 30 (300%) | | | | |
| TLL-SH | | | | 1% (V/W) of HCO | | | | |
| AV (72 h) | 177.71 | 181.06 | 180.59 | 181.01 | 181.55 | 183.57 | 179.85 | 178.66 |
| Hydrolysis rate, % | 94.03 | 95.81 | 95.56 | 95.78 | 96.07 | 97.15 | 94.64 | 94.53 |

By optimizing ratios and reaction conditions, hydrolysis products with AV higher than 175 could be easily obtained with a dosage of 1% TLL-SH.

4.2 the Effect of TLL-SH Dosage to HCO Hydrolysis 5 grams of HCO in fine powder form was put in the reactor, then different amount of n-hexane as shown in the table was added to individual reactor. Different amount of deionized water as shown in the table was then added. 100 µL, 50 µL or 25 µL (2%, 1% or 0.5% of (V/W) of HCO) of TLL-SH was added. The mixture was heated with a stirring rate of 450 rpm to the reaction temperature of 37 or 50° C. The stirring was continued through the reaction, and the reaction was undertaken at the same temperature for 72 hours. After the completion of the reaction, the acid values were determined and the hydrolysis rates were calculated.

TABLE 33

TLL-SH dosages for the HCO hydrolysis with n-hexane

| Exp. No. | 7 | 161 | 162 |
|---|---|---|---|
| HCO powder | | 5 g | |
| n-Hexane | 25 mL | 15 mL | 15 mL |
| H2O | 1.25 mL | 3.75 mL | 3.75 mL |
| TLL-SH, µL (% (V/W) of HCO) | 100 (2%) | 50 (1%) | 25 (0.5%) |
| Temp. (° C.) | 37 | 50 | 50 |
| AV (72 h) | 175.66 | 182.22 | 171.15 |
| Hydrolysis rate, % | 92.94 | 96.43 | 90.54 |

Example 5—Comparative Experiments with Bi-Enzyme and Bi-Organic Solvent System 10 grams of HCO in the form of flake was put into the reactor, then 40 mL of deionized water was added (400% (V/W) of the HCO weight), and 40 mL of organic solvent or organic solvent mixture (the ratio of "the volume of organic solvent in mL to the weight of oil in gram (V/W)" was 400%) was added to the reactor according to the Table 34. Then different amount of enzyme(s) was added into the mixture according to the Table 34 below. The mixture was heated with a stirring rate of 450 rpm to the reaction temperature of 45° C. The stirring was continued through the reaction, and the reaction time was 24 hours. After the completion of the reaction, the acid values were determined and the hydrolysis rates were calculated.

TABLE 34

| Comparative experiments | | | | | | | |
|---|---|---|---|---|---|---|---|
| Exp. No. | 163 | 164 | 165 | 166 | 167 | 168 | 169 |
| Organic solvent, (mL) | acetone/n-hexane (16 + 24) | isooctane (40) | n-hexane (40) | isooctane (40) | n-hexane (40) | isooctane (40) | acetone/n-hexane (16 + 24) |
| μL of Enzyme (V/W % of HCO) | 200 Eversa (2%) | 200 TLL-SH (2%) + 200 G50-SH (2%) | 200 TLL-SH (2%) + 200 G50-SH (2%) | 200 Eversa (2%) | 400 Eversa (4%) | 400 Eversa (4%) | 200 TLL-SH (2%) + 200 G50-SH (2%) |
| AV (24 h) | 148.79 | 135.35 | 98.65 | 151.37 | 159.37 | 166.51 | 127.62 |
| Hydrolysis rate, % | 78.64 | 71.50 | 51.95 | 80.01 | 84.27 | 88.07 | 67.37 |

Example 6—Melting HCO and Conducting Hydrolysis Under Different Temperature 2.5 mL of deionized water and 15 mL of isooctane were added into a reactor. The mixture was chilled to 4° C. HCO was melted at 95° C. and slowly added to the chilled mixture while stirring. The reaction mixture was brought to the desired reaction temperature (Table 35) while stirring at 450 rpm. 15 μL of EVERSA was then added to the reactor and the stirring was continued through the reaction. The reaction time was 72 hours. After the completion of the reaction, the acid values were determined and the hydrolysis rates were calculated.

TABLE 35

| Hydrolysis under different temperatures by adding melted HCO substrate | | | | |
|---|---|---|---|---|
| Exp. No. | 170 | 171 | 172 | 173 |
| Eversa, % (V/W) of HCO | 15 μL, (0.234%) | 15 μL, (0.283%) | 15 μL, (0.283%) | 15 μL, (0.283%) |
| HCO liquid (g) | 6.4 | 5.3 | 5.3 | 5.3 |
| Isooctane | | 15 mL | | |
| H20 | | 2.5 mL | | |
| AV (72 h) | 139.64 | 155.28 | 168.70 | 154.83 |
| Hydrolysis rate, % | 73.77 | 82.09 | 89.23 | 81.85 |
| Temp. (° C.) | 40 | 45 | 50 | 55 |

Example 7—Adding HCO in the Form of Flake Vs in the Form of Powder

HCO powder was prepared by breaking the HCO flake into fine powder with a size of smaller than 0.5 millimeter in diameter with a home blender. The size of the HCO powder was examined by using optical microscope and sieving method. HCO in flake or powder form was added to a reactor with water, n-hexane and EVERSA respectively according to Table 36 below. The stirring was continued through the reaction, and the reaction time is 72 hours at 40° C. The acid values were then determined and the hydrolysis rates were calculated. Results are shown in Table 36.

TABLE 36

| Adding HCO in flake form vs. in powder form | | |
|---|---|---|
| Exp. No. | 174 | 175 |
| HCO, g | 20 (flake) | 40 (powder) |
| Eversa, μL (% (V/W) of HCO) | 300 (1.5%) | 400 (1%) |
| H₂O, mL (% (V/W) of HCO) | 3 (15%) | 6 (15%) |
| n-Hexane, mL (% (V/W) of HCO) | 40 (200%) | 80 (200%) |
| AV (72 h) | 175.0 | 177.0 |
| Hydrolysis rate, % | 92.59 | 93.65 |

When HCO fine powder form was used as substrate, higher acid value of hydrolysis product was achieved even with a lower enzyme dosage compared with the flake form wherein a higher enzyme dosage was used. The result indicates that the hydrolysis is more efficient when fine powder form HCO is used.

Example 8—Adding Enzyme in Batches

Experiment No. 176:100 g of HCO in the form of fine powder was put into the reactor, then 50 mL deionized water was added, and 200 mL of isooctane were added into the reactor. Then 300 μL of EVERSA (0.3% (V/W) of HCO) was added into the mixture. The mixture is heated with a stirring rate of 450 rpm to the reaction temperature of 50° C. The stirring was continued through the reaction, and the reaction time was 70 hours. After the completion of the reaction, the acid values were determined to be 154.88. If add another 0.1% EVERSA, and let the hydrolysis being carried out for another 24 hours, an acid value of 175.68 was achieved.

Example 9-Palm Stearin (IV15, Melting Point 56-61° C.; IV35, Melting Point 47-55° C.; IV38, Melting Point 32-49° C.)

The hydrolysis of three kinds of palm stearins with different iodine value (IV15, IV35 and IV38) was studied. The experiments were set up as shown in Table 37 and 38 below. 10 grams of palm stearin was mixed with 30 mL of n-hexane and 7.5 mL of deionized water (including the water present in the enzyme). Different amount of EVERSA was added according to the tables. The mixture was heated with a stirring rate of 450 rpm to the reaction temperature of 50° C. The stirring was continued through the reaction, and the reaction time was 72 hours. After the completion of the reaction, the acid values were determined and the hydrolysis rates were calculated as shown in Table 37 and Table 38.

TABLE 37

Hydrolysis of palm stearins by different dosages of Eversa

| Exp. No. | 177 | 178 | 179 | 180 | 181 | 182 |
|---|---|---|---|---|---|---|
| Palm stearin | IV15, 10 g | IV15, 10 g | IV35, 10 g | IV35, 10 g | IV38, 10 g | IV38, 10 g |
| H₂O, mL (% (V/W) of palm stearin) | | | 7.5 (75%) | | | |
| n-Hexane, mL (% (V/W) of palm stearin) | | | 30 (300%) | | | |
| Eversa (% (V/W) of palm stearin) | 50 μL (0.5%) | 100 μL (1%) | 50 μL (0.5%) | 100 μL (1%) | 50 μL (0.5%) | 100 μL (1%) |
| Temp. | | | 50° C. | | | |
| AV (72 h) | 89.22 | 131.64 | 54.37 | 112.98 | 141.79 | 154.29 |
| Hydrolysis rate, % | 40.98 | 60.77 | 25.05 | 53.11 | 67.33 | 73.29 |

TABLE 38

Hydrolysis of palm oil stearins by high dosage of Eversa

| Exp. No. | 183 | 184 | 185 |
|---|---|---|---|
| Palm stearin | IV15, 10 g | IV35, 10 g | IV38, 10 g |
| H₂O, mL (% (V/W) of palm stearin) | | 7.5 (75%) | |
| n-Hexane, mL (% (V/W) of palm stearin) | | 30 (300%) | |
| Eversa (% (V/W) of palm stearin) | 500 μL (5%) | 500 μL (5%) | 500 μL (5%) |
| Temp. | | 50° C. | |
| AV (72 h) | 202.97 | 153.86 | 204.88 |
| Hydrolysis rate, % | 94.03 | 72.68 | 97.41 |

Example 10—Lard (Melting Point 28° C.-44° C.)

The hydrolysis of lard was studied. The experiments were set up as shown in the table below. 10 grams of lard was mixed with 30 mL of n-hexane and 7.5 mL of deionized water (including the water present in the enzyme). Different amount of EVERSA (50 μL or 100 μL, corresponding to 0.5% or 1% (V/W) of lard) was added according to the table. The mixture was heated with a stirring rate of 450 rpm to the reaction temperature of 50° C. The stirring was continued through the reaction, and the reaction time was 72 hours. After the completion of the reaction, the acid values were determined and the hydrolysis rates were calculated and shown in the table below.

TABLE 39

Hydrolysis of lard by different dosages of Eversa

| Exp. No. | 185 | 186 |
|---|---|---|
| Lard | | 10 g |
| H₂O, mL (% of lard) | | 7.5 (75%) |
| n-Hexane, mL (% (V/W) of lard) | | 30 (300%) |
| Eversa (% (V/W) of lard) | 50 μL (0.5%) | 100 μL (1%) |
| Temp. | | 50° C. |
| AV (72 h) | 147.36 | 164.99 |
| Hydrolysis rate, % | 71.56 | 79.68 |

Example 11—Preparation of TLL-SH and G50-SH

11.1 Expression Vector Construction

*Thermomyces lanuginosus* lipase (TLL-SH) and *Penicillium* camemberti lipase (G50-SH) were codon optimized according to *Pichia pastoris* preference and synthesized by Sangon Biotech (Shanghai) Co., Ltd. with an EcoRI restriction enzyme site (GAATTC) at the 3' end of each gene. The sequences of two lipase genes were list in SEQ NO. 1 and SEQ NO. 2, which contain underlined a-factor signal peptide sequence before the nucleic acid coding for the mature peptide.

Lipase gene fragments were respectively ligated after *Pichia pastoris* AOX1 promoter, from commercial plasmid pAO815, by overlapping polymerase chain reaction (PCR). The overlapping PCR product and pAO815 plasmid were double digested by AatII and EcoRI to construct the recombinant vector pAO-TLL-SH and pAO-G50-SH.

11.2 Recombinant *Pichia pastoris* Strain Construction and Expression

*Pichia pastoris* GS115 host (Invitrogen, C181-00) was used for the transformation of recombinant vectors pAO-TLL-SH and pAO-G50-SH. Then activity display plates (MYO plates: 1% Yeast nitrogen base, 1% methanol, 3% olive oil, 0.37% Poly (vinyl alcohol), 10 μg/mL Rhodamine B indicator, 2% agar for TLL-SH. MYP: 1% Yeast nitrogen base, 1% methanol, 1% Polysorbate 80, 10 μg/mL Rhodamine B indicator, 2% agar for G50-SH) were used for screening positive transformants. Recombinant colony with biggest hydrolysis circle was selected for enzyme production. Fermentation and enzyme recovery process were carried out as described in CN 106884009A.

```
Thermomyces lanuginosus lipase sequence (TLL-SH)
                                         SEQ. NO. 1
atgagatttccttcaattttttactgcagttttattcgcagcatcctccgca ttagctgctccagtcaacactacaacagaagatgaaacggcacaaattccg gctgaagctgtcatcggttactcagatttagaaggggatttcgatgttgct gttttgccatttccaacagcacaaataacgggttattgtttataaatact actattgccagcattgctgctaaagaagaaggggtatctcttgagaaaaga gaggctgaagctgaagtctctcaagacttgttcaaccagttcaacttgttc gctcaatactctgccgctgcctactgtggtaagaacaatgatgctccagct
```

```
ggtactaacattacctgtactggtaacgcttgtccagaagttgagaaggct gatgctaccttcctgtactccttcgaagactctggagttggagatgttact ggtttcctggccttggataacactaacaagttgatcgttctgtccttcaga ggttccagatccatcgagaactggattggtaacttgaactttgacttgaag gagatcaacgacatctgttctggatgtcgtggtcacgatggatttacctcc tcttggagatctgttgctgataccttgagacagaaggtcgaagatgctgtc agagaacatccagactatagagttgtcttcactggtcactccttgggaggt gccttggctactgttgctggtgctgacttgcgtggtaatggttatgacatt gatgtcttctcctacggtgctccaagagttggtaatcgtgccttcgctgag tttctgaccgtccaaactggaggtactttgtacagaattacccatactaac gacattgttccaagattgccaccacgtgagttcggatactctcattcctct ccagagtactggatcaagtctggaaccttggttccagtcactcgtaacgac atcgtcaagattgaaggtattgatgccactggaggtaacaatcaaccaaac attccagacattccagctcacttgtggtactttggtctgattggtacttgc ttgtaa*GAATTC*

*Penicillium camemberti* lipase sequence (G50-SH)

SEQ. NO. 2

<u>ATGAGATTTCCTTCAATTTTTACTGCAGTTTTATTCGCAGCATCCTCCGCA</u>

<u>TTAGCTGCTCCAGTCAACACTACAACAGAAGATGAAACGGCACAAATTCCG</u>

<u>GCTGAAGCTGTCATCGGTTACTCAGATTTAGAAGGGGATTTCGATGTTGCT</u>

<u>GTTTTGCCATTTTCCAACAGCACAAATAACGGGTTATTGTTTATAAATACT</u>

<u>ACTATTGCCAGCATTGCTGCTAAAGAAGAAGGGGTATCTCTTGAGAAAAGA</u>

<u>GAGGCTGAAGCT</u>GATGTCTCCACTTCCGAACTGGACCAGTTCGAGTTCTGG

GTTCAATACGCAGCCGCCTCTTACTACGAGGCTGATTACACCGCACAGGTT

GGTGATAAGCTGTCCTGCTCTAAGGGTAACTGCCCAGAAGTTGAAGCAACC

GGTGCAACTGTGTCTTACGACTTCTCCGATTCCACGATCACTGACACCGCA

GGTTACATCGCAGTTGATCACACCAACTCCGCAGTGGTACTGGCATTCCGT

GGTTCTTACTCCGTACGTAACTGGGTTGCTGATGCTACTTTCGTCCATACC

AACCCAGGTCTGTGTGATGGTTGTCTGGCTGAGCTGGGTTTCTGGTCTTCC

TGGAAGCTGGTTCGTGATGATATTATCAAAGAACTGAAAGAAGTGGTGGCA

CAGAACCCAAACTATGAACTGGTGGTCGTGGGCCACTCCCTGGGTGCTGCT

GTGGCTACTCTGGCTGCTACCGACCTGCGTGGTAAAGGTTATCCATCTGCT

AAACTGTACGCTTACGCTTCCCCTCGTGTTGGCAACGCAGCCCTGGCCAAA

TATATCACCGCCCAGGGCAACAACTTCCGTTTCACCCACACCAATGACCCA

GTACCTAAACTGCCACTGCTGTCTATGGGCTATGTACATGTTTCTCCTGAA

TATTGGATCACCTCTCCTAACAACGCCACTGTTTCTACCTCTGACATCAAA

GTCATTGACGGCGACGTATCTTTTGACGGCAATACCGGCACGGGCCTGCCT

CTGCTGACGGACTTTGAAGCCCACATTTGGTACTTTGTACAGGTTGACGCC

GGCAAAGGTCCTGGCCTGCCATTCAAACGTGTTTAAG*AATTC*
```

The invention claimed is:

1. A process of hydrolyzing hydrogenated castor oil to obtain 12-hydroxystearic acid, the process comprising a step of mixing water, an organic solvent, and a lipase with the hydrogenated castor oil to form a mixture, and a step of hydrolyzing the hydrogenated castor oil in the mixture to obtain 12-hydroxystearic acid with an acid value of higher than 160,
wherein the lipase comprises one or more lipases from *Thermomyces* sp. or a derivative of the one or more lipases from *Thermomyces* sp. with less than 20 amino acids substituted, deleted, or added to the one or more lipases from *Thermomyces* sp., the lipase excludes any monoacylglycerol lipase or any lipase from *Rhizomucor* sp., and the organic solvent is selected from a group consisting of a sterically hindered alcohol, a non-polar organic solvent, and a mixture of a water-miscible organic solvent with a non-polar organic solvent.

2. The process of claim 1, wherein the *Thermomyces* sp. is *Thermomyces lanuginosus*.

3. The process of claim 1, wherein the one or more lipases from *Thermomyces* sp. or the derivative is provided in solid form or in liquid solution form.

4. The process of claim 1, wherein the one or more lipases from *Thermomyces* sp. or the derivative is added once or in batch.

5. The process of claim 1, wherein the hydrogenated castor oil is melted or ground to a powder form before the step of mixing.

6. The process of claim 1, wherein
(i) the non-polar organic solvent is a saturated hydrocarbon containing 5 to 12 carbons or methyl tert-butyl ether (MTBE);
(ii) the steric hindered alcohol is tert-butanol (t-BuOH);
(iii) the water-miscible organic solvent is selected from acetone, tert-butanol and their mixture; and
(iv) in the mixture of a water-miscible organic solvent with a non-polar organic solvent, the volume ratio of the water-miscible organic solvent to the non-polar organic solvent is from 20:80 to 50:50.

7. The process of claim 1, wherein the step of hydrolyzing the hydrogenated castor oil is conducted under a temperature of 30° C. to 60° C.

8. The process of claim 1, wherein glycerol is generated during the step of hydrolyzing hydrogenated castor oil.

9. The process of claim 1, wherein the hydrolysis product has an acid value of higher than 165.

10. The process of claim 1, wherein if the one or more lipases from *Thermomyces* sp. or the derivative is provided in liquid solution form, the ratio for the volume of the one or more lipases from *Thermomyces* sp. or the derivative in mL to the weight of the hydrogenated castor oil in grams is not less than 0.2%; if the one or more lipases from *Thermomyces* sp. or the derivative is provided in solid form, the weight ratio of the one or more lipases from *Thermomyces* sp. or the derivative to the weight of the hydrogenated castor oil is not less than 50 ppm of the hydrogenated castor oil.

11. The process of claim 1, wherein the weight ratio of the water and the hydrogenated castor oil is from 15% to 300% or the ratio of the volume of the organic solvent in mL to the weight of the hydrogenated castor oil in grams is more than 75%.

12. The process of claim 8 further comprising removing water, the glycerol, and the organic solvent after the step of hydrolyzing the hydrogenated castor oil.

13. The process of claim 10, wherein if the one or more lipases from *Thermomyces* sp. or the derivative is provided in liquid solution form, the ratio for the volume of the one or more lipases from *Thermomyces* sp. or the derivative in mL to the weight of the hydrogenated castor oil in grams is from 0.3% to 2%; if the one or more lipases from *Thermomyces* sp. or the derivative is provided in solid form, the weight ratio of the one or more lipases from *Thermomyces* sp. or the derivative to the weight of the hydrogenated castor oil is not less than 75 ppm of the hydrogenated castor oil.

14. The process of claim 11, wherein the weight ratio of the water and the hydrogenated castor oil is from 30% to 250% or from 100% to 300%.

15. The process of claim 11, wherein the ratio of the volume of the organic solvent in mL to the weight of the hydrogenated castor oil in grams is between 100% and 500%.

* * * * *

SEQUENCE LISTING

<160> NUMBER OF SEQ ID NOS: 2

<210> SEQ ID NO 1
<211> LENGTH: 1083
<212> TYPE: DNA
<213> ORGANISM: Artificial Sequence
<220> FEATURE:
<223> OTHER INFORMATION: Codon optimised Thermomyces lanuginosus lipase
      gene sequence

<400> SEQUENCE: 1
atgagatttc cttcaatttt tactgcagtt ttattcgcag catcctccgc attagctgct     60
ccagtcaaca ctacaacaga agatgaaacg gcacaaattc cggctgaagc tgtcatcggt    120
tactcagatt tagaagggga tttcgatgtt gctgttttgc catttccaa cagcacaaat    180 aacgggttat tgtttataaa tactactatt gccagcattg ctgctaaaga agaaggggta    240
tctcttgaga aaagagaggc tgaagctgaa gtctctcaag acttgttcaa ccagttcaac    300
ttgttcgctc aatactctgc cgctgcctac tgtggtaaga caatgatgc tccagctggt    360 actaacatta cctgtactgg taacgcttgt ccagaagttg agaaggctga tgctaccttc    420
ctgtactcct cgaagactc tggagttgga gatgttactg gtttcctggc cttggataac    480
actaacaagt tgatcgttct gtccttcaga ggttccagat ccatcgagaa ctggattggt    540
aacttgaact ttgacttgaa ggagatcaac gacatctgtt ctggatgtcg tggtcacgat    600
ggatttacct cctcttggag atctgttgct gataccttga gacagaaggt cgaagatgct    660
gtcagagaac atccagacta tagagttgtc ttcactggtc actccttggg aggtgccttg    720

```
gctactgttg ctggtgctga cttgcgtggt aatggttatg acattgatgt cttctcctac    780
ggtgctccaa gagttggtaa tcgtgccttc gctgagtttc tgaccgtcca aactggaggt    840
actttgtaca gaattaccca tactaacgac attgttccaa gattgccacc acgtgagttc    900
ggatactctc attcctctcc agagtactgg atcaagtctg gaaccttggt tccagtcact    960
cgtaacgaca tcgtcaagat tgaaggtatt gatgccactg gaggtaacaa tcaaccaaac   1020
attccagaca ttccagctca cttgtggtac tttggtctga ttggtacttg cttgtaagaa   1080
ttc                                                                 1083

<210> SEQ ID NO 2
<211> LENGTH: 1113
<212> TYPE: DNA
<213> ORGANISM: Artificial Sequence
<220> FEATURE:
<223> OTHER INFORMATION: Codon optimised Penicillium camemberti lipase
      gene sequence

<400> SEQUENCE: 2
atgagatttc cttcaatttt tactgcagtt ttattcgcag catcctccgc attagctgct     60
ccagtcaaca ctacaacaga agatgaaacg gcacaaattc cggctgaagc tgtcatcggt    120
tactcagatt tagaagggga tttcgatgtt gctgttttgc cattttccaa cagcacaaat    180
aacgggttat tgtttataaa tactactatt gccagcattg ctgctaaaga agaaggggta    240
tctcttgaga aaagagaggc tgaagctgat gtctccactt ccgaactgga ccagttcgag    300
ttctgggttc aatacgcagc cgcctcttac tacgaggctg attacaccgc acaggttggt    360
gataagctgt cctgctctaa gggtaactgc ccagaagttg aagcaaccgg tgcaactgtg    420
tcttacgact tctccgattc cacgatcact gacaccgcag gttacatcgc agttgatcac    480
accaactccg cagtggtact ggcattccgt ggttcttact ccgtacgtaa ctgggttgct    540
gatgctactt tcgtccatac caacccaggt ctgtgtgatg gttgtctggc tgagctgggt    600
ttctggtctt cctggaagct ggttcgtgat gatattatca agaactgaa agaagtggtg    660 gcacagaacc caaactatga actggtggtc gtgggccact ccctgggtgc tgctgtggct    720
actctggctg ctaccgacct gcgtggtaaa ggttatccat ctgctaaact gtacgcttac    780
gcttcccctc gtgttggcaa cgcagccctg gccaaatata tcaccgccca gggcaacaac    840
ttccgtttca cccacaccaa tgacccagta cctaaactgc cactgctgtc tatgggctat    900
gtacatgttt ctcctgaata ttggatcacc tctcctaaca acgccactgt ttctacctct    960
gacatcaaag tcattgacgg cgacgtatct tttgacggca ataccggcac gggcctgcct   1020
ctgctgacgg actttgaagc ccacatttgg tactttgtac aggttgacgc cggcaaggt   1080 cctggcctgc cattcaaacg tgtttaagaa ttc                                1113
```